US007638331B2

(12) United States Patent
Godbey et al.

(10) Patent No.: US 7,638,331 B2
(45) Date of Patent: Dec. 29, 2009

(54) DIRECTED APOPTOSIS IN COX-2 OVEREXPRESSING CANCER CELLS THROUGH EXPRESSION TARGETED GENE DELIVERY

(75) Inventors: W. Terrance Godbey, New Orleans, LA (US); Anthony Atala, Winston-Salem, NC (US)

(73) Assignee: The Administration of the Tulane Rducation Fund, New Orleans, LA (US)

( * ) Notice: Subject to any disclaimer, the term of this patent is extended or adjusted under 35 U.S.C. 154(b) by 538 days.

(21) Appl. No.: 11/023,020

(22) Filed: Dec. 23, 2004

(65) Prior Publication Data
US 2005/0187177 A1 Aug. 25, 2005

Related U.S. Application Data

(60) Provisional application No. 60/533,965, filed on Jan. 2, 2004.

(51) Int. Cl.
C12N 15/00 (2006.01)
C12N 15/06 (2006.01)
C12N 15/11 (2006.01)
C12N 15/86 (2006.01)
C12N 15/87 (2006.01)

(52) U.S. Cl. .............. 435/440; 435/455; 435/456; 435/458; 435/320.1; 435/465

(58) Field of Classification Search .................. None
See application file for complete search history.

(56) References Cited

U.S. PATENT DOCUMENTS 6,025,194 A 2/2000 Funk
6,224,866 B1 5/2001 Barbera-Guillem
6,344,323 B1 2/2002 Seifer
6,384,051 B1 5/2002 Frost et al.
6,395,502 B1 5/2002 Jakobsson et al.
6,403,630 B1 6/2002 Dannenberg et al.
6,432,979 B1 8/2002 Frost et al.
6,469,053 B1 10/2002 Romanczyk, Jr. et al.

(Continued)

FOREIGN PATENT DOCUMENTS

| EP | 1201766 | 5/2002 |
| WO | WO 95/02684 | 1/1995 |
| WO | WO 99/04030 | 1/1999 |
| WO | WO 99/50425 | * 10/1999 |

OTHER PUBLICATIONS

Xie et al. (2001) Cancer Res. 61:6795-6804.*
Tai et al. (1999) Cancer Res. 59:2121-2126.*
Casado et al. (2001) Clin. Cancer Res. 7:2496-2504.*
Wesseling et al. (2001) Cancer Gene Ther. 8:990-996.*
Ogris et al (1999) Gene Ther. 6:595-605.*

(Continued)

Primary Examiner—Maria B Marvich
(74) Attorney, Agent, or Firm—Thomas J. Engellenner; Nutter McClennen & Fish, LLP

(57) ABSTRACT

The present invention provides methods and constructs for selectively expressing an Apoptosis-Inducing Gene (AIG) in a population of cells that overexpress cyclooxygenase-2 (COX-2) to induce apoptosis in the cell. To achieve this goal a chimeric gene construct is used that comprises a cyclooxygenase-2 promoter (COX-2 promoter) that is operably linked to at least one AIG such that the COX-2 promoter is activated in cells that overexpress COX-2, thereby resulting in transcription and translation of the AIG, which in turn activates apoptosis in the cell. Thus, apoptosis is selectively induced in only those cells capable of overexpressing COX-2.

40 Claims, 13 Drawing Sheets

U.S. PATENT DOCUMENTS

| | | | |
|---|---|---|---|
| 6,492,332 | B1 | 12/2002 | Demopulos et al. |
| 6,500,434 | B1 | 12/2002 | Langermann et al. |
| 6,511,970 | B1 | 1/2003 | Rodriguez |
| 6,534,540 | B2 | 3/2003 | Kindness et al. |
| 6,541,519 | B2 | 4/2003 | Collin et al. |
| 6,548,540 | B2 | 4/2003 | Kennedy |
| 6,552,075 | B2 | 4/2003 | Gribble et al. |
| 6,573,290 | B1 | 6/2003 | Love |
| 6,573,292 | B1 | 6/2003 | Nardella |
| 6,579,895 | B2 | 6/2003 | Karim et al. |
| 6,589,987 | B2 | 7/2003 | Kennedy |
| 6,593,361 | B2 | 7/2003 | Kargman et al. |
| 2002/0015739 | A1 | 2/2002 | Wu |
| 2002/0055457 | A1 | 5/2002 | Janus et al. |
| 2002/0081705 | A1* | 6/2002 | Mankovich ............. 435/226 |
| 2002/0187502 | A1 | 12/2002 | Waterman et al. |
| 2003/0022811 | A1 | 1/2003 | Singh et al. |
| 2003/0035790 | A1 | 2/2003 | Chen et al. |
| 2003/0045694 | A1 | 3/2003 | Chait et al. |
| 2003/0064493 | A1 | 4/2003 | Jakobsson et al. |
| 2003/0082141 | A1 | 5/2003 | O'Connor |
| 2003/0096777 | A1 | 5/2003 | Besterman et al. |
| 2003/0113303 | A1 | 6/2003 | Schwartz |
| 2003/0125615 | A1 | 7/2003 | Schwartz |
| 2003/0129750 | A1 | 7/2003 | Schwartz |
| 2003/0133932 | A1 | 7/2003 | Zhou et al. |
| 2003/0157061 | A1 | 8/2003 | Bennett |
| 2003/0157084 | A1 | 8/2003 | Jakobsson et al. |
| 2003/0157113 | A1 | 8/2003 | Terman |
| 2003/0162829 | A1 | 8/2003 | Kindness et al. |
| 2003/0165956 | A1 | 9/2003 | Stevens et al. |

OTHER PUBLICATIONS

UniProtKB/Swiss-Prot entry for P35354, http://ca.expasy.org/uniprot/P35354, downloaded Nov. 14, 2007.*

Perfettini and Kroemer, Caspase activation is not death, Nature Immunology, vol. 4 (4) Apr. 2003, pp. 308-310.*

Overview: Regulation of Apoptosis, Cell signaling Technology, 2002, downloaded Oct. 19, 2008.*

Gurtu, V. et al., Activation of ICE-Family Leads to Various Phenotypes in Apoptic Cells, CLONTECHniques (Jul. 1997), pp. 28-30.

McCormick, F., Cancer Gene Therapy: Fringe or Cutting Edge? (Nov. 2001), Nature Reviews: Cancer, vol. 1, pp. 130-141.

Salvesen, G. et al., Caspase activation: The induced-proximity model, Proc. Natl. Acad. Sci. (Sep. 1999), Vol. 96, pp. 10964-10967.

Steiner, M. et al., Gene Therapy for prostate cancer, Gene Ther Mol Biol vol. 4, pp. 233-248, 1999.

Verhaegh, G., et al., Isolation and Characterization of the Promoter of the Human Prostate Cancer-specific DD3 Gene, J. Biol. Chem. (Dec. 1999), vol. 275, Issue 48, pp. 37496-37503.

* cited by examiner solid black bar =HFF cells
white bar =PC3 cells
striped bar=HBT5 cells

SEQUENCE LISTING

```
<160> NUMBER OF SEQ ID NOS: 5

<210> SEQ ID NO 1
<211> LENGTH: 5
<212> TYPE: PRT
<213> ORGANISM: Homo sapiens
<220> FEATURE:
<221> NAME/KEY: Xaa
<222> LOCATION: (4)..(4)
<223> OTHER INFORMATION: Xaa can be any one of Arg, Gln, Glu or Gly
```

```
<220> FEATURE:
<221> NAME/KEY: misc_feature
<222> LOCATION: (4)..(4)
<223> OTHER INFORMATION: Xaa can be any naturally occurring amino acid

<400> SEQUENCE: 1

Gln Ala Cys Xaa Gly
1               5

<210> SEQ ID NO 2
<211> LENGTH: 27
<212> TYPE: DNA
<213> ORGANISM: Homo sapiens

<400> SEQUENCE: 2
ttcaaatgag attgtgggaa aattgct                                          27

<210> SEQ ID NO 3
<211> LENGTH: 24
<212> TYPE: DNA
<213> ORGANISM: Homo sapiens

<400> SEQUENCE: 3
agatcatctc tgcctgagta tctt                                             24

<210> SEQ ID NO 4
<211> LENGTH: 19
<212> TYPE: DNA
<213> ORGANISM: Homo sapiens

<400> SEQUENCE: 4
tcaccatctt ccaggagcg                                                   19

<210> SEQ ID NO 5
<211> LENGTH: 20
<212> TYPE: DNA
<213> ORGANISM: Homo sapiens

<400> SEQUENCE: 5
ctgcttcacc accttcttga                                                  20
```

DIRECTED APOPTOSIS IN COX-2 OVEREXPRESSING CANCER CELLS THROUGH EXPRESSION TARGETED GENE DELIVERY

PRIORITY INFORMATION

This application claims priority to U.S. provisional application No. 60/533,965, filed Jan. 2, 2004, the entire content of which is incorporated by reference.

GOVERNMENT SUPPORT

This invention was made with government support under R01-DK57260 awarded by the National Institute of Health. The government has certain rights in the invention.

FIELD OF THE INVENTION

The present invention provides methods and constructs for selectively expressing at least one Apoptosis-Inducing Gene (AIG). The selective expression of the AIG in the cell activates the apoptotic pathway and causes cell destruction.

BACKGROUND OF THE INVENTION

An ideal cancer therapy would be a treatment that causes all cancer cells to disappear, leaving behind only healthy, untransformed tissue. The technology of gene transfer has been proposed towards this end, whereby cancer cells themselves are harnessed to produce a fatal protein which causes their own demise. However, simply having tumor cells produce a fatal toxin is not sufficient to achieve the stated goal, however, because of lingering effects upon neighboring cells following cancer cell death. For example, the release of the toxic gene product into the extracellular space following necrotic cell death can cause a severe bystander effect resulting in harm to neighboring tissue. Thus, a more desirable process resulting in cell death is apoptosis, where cells shut down without the bystander effect.

Apoptosis, also referred to as physiological cell death or programmed cell death, is a normal physiological process of cell death that plays a critical role in the regulation of tissue homeostasis by ensuring that the rate of new cell accumulation produced by cell division is offset by a commensurate rate of cell loss due to death. Apoptosis can be characterized by morphological changes in the cell, including fragmentation of nuclear chromatin, compaction of cytoplasmic organelles, dilatation of the endoplasmic reticulum, a decrease in cell volume and alterations to the plasma membrane, resulting in the recognition and phagocytosis of apoptotic cells and prevention of an inflammatory response.

Gene delivery has been used in the past in an attempt to treat various cancers (Rubin et al. (1997) *Gene Ther.* 4: 419-425 and Vogelzang et al. (1994) *Hum Gene Ther.* 5: 1357-1370). However, independent of bystander effects, the use of many gene delivery methods adversely affects healthy, untransformed cells due to indiscriminant transfection of all cell types in a given area. A method to selectively target cancer cells for treatment is desirable, but the similarity of transformed cells to normal somatic cells makes this objective extremely difficult to achieve. Although the attachment of ligands to gene delivery complexes is a method that has yielded some progress in targeted gene delivery to normal tissues (Hood et al. (2002) *Science* 296: 2404-2407), this method has not produced much direct success with cancer cells because, in part, of the similarities between the receptors expressed by tumor cells and the tissues from which they originated. Commonalities between tumor cells, which are also unique to tumor cells, are continually being sought.

Previous published work includes the delivery of genes coding for caspases, which can induce apoptosis using a prostate specific composite promoter, $ARR_2PB_2$. (See Xie et al. (2001) *Cancer Res.* 61: 6795-6804; and Shariat et al. (2001) *Cancer Res.* 61: 2562-2571). This work demonstrated tissue-specific targeting and induction of apoptosis in prostate cancer cells, by placing the caspase transgene under the transcriptional control of a tissue-specific promoters, which are functional in prostate cancer cells rather than all cells.

Several pro-drug activation genes have also been studied for application in cancer gene therapy. In one example, herpes simplex virus thymidine kinase (HSV-TK) in combination with the pro-drug ganciclovir represents a prototypic pro-drug/enzyme activation system known in the art with respect to its potential applications in cancer gene therapy. HSV-TK phosphorylates the pro-drug ganciclovir and generates nucleoside analogs that induce DNA chain termination and cell death in actively dividing cells. Tumor cells transduced with HSV-TK acquire sensitivity to ganciclovir, a clinically proven agent originally designed for treatment of viral infections. (Moolten et al. (1990) *Natl. Cancer Inst.* 82:297-300; Ezzeddine et al., (1991) *New Biol.* 3:608-614). The pro-drug-TK approach was also reported by Yamamoto et al. in which the COX-2 promoter was used to reduce the level of toxicity due to thymidine kinase gene delivery in the liver ((2001) *Mol Ther.* 3: 385-394). However, this work relies on the complex activation of a pro-drug.

The heightened COX-2 expression in cancer cells has been used in the past as a form of cancer treatment by COX-2 inhibitors that cause inhibition of COX-2 (Elder et al. (1997) *Clin Cancer Res.* 3:1679-1683). COX-2 inhibitors are already on the market to combat inflammation, sold under the trade names Vioxx™ and Celebrex™. However, to date, the prior art only speaks of altering COX-2 levels, it does not address using elevated levels of COX-2 as a means of targeting a specific population of cells to induce apoptosis.

Accordingly, a need exists for specifically targeting cancer cells and inducing apoptosis in such cells. A need also exists for targeted gene therapy at the DNA level, through the use of appropriate promoters, such that entire classes of cells can be treated with one transfection.

SUMMARY OF THE INVENTION

The present invention is based, in part, on the discovery of a chimeric gene construct composed of a COX-2 promoter operably linked to at least one apoptosis-inducing gene that can cause selectively induced apoptosis in a population of diseased cells, such as cells with elevated levels of COX-2, or cells with elevated levels of a molecule or protein associated with inflammation. The invention thus permits targeted gene therapy to cells that exhibit elevated COX-2 levels or cells with an elevated inflammatory protein, and results in the killing and destruction of these cells rather than the general population of cells. In one aspect, the invention relies on the principle that the promoter is active only in those cells that overexpress COX-2 or the inflammatory protein. The methods and constructs of the invention thereby provide a selective method of targeting specific cells relying on promoter based induction of apoptosis.

Accordingly, in one aspect, the invention pertains to a chimeric gene construct comprising an upstream regulatory element operably linked to an apoptosis-inducing gene. The expression of the apoptosis-inducing gene is driven by the upstream regulatory element, and the apoptosis-inducing gene is expressed in a cell that overexpresses a protein, such as an inflammatory protein (e.g., IL-2, IL-21 and IL-23) which activates the upstream regulatory element, such that self-induced apoptosis occurs in the cell.

The chimeric gene construct can further comprise a delivery vehicle such as a non-viral delivery vehicle or a viral delivery vehicle. Examples of non-viral delivery vehicle include, but are not limited to, poly(ethylenimine) (PEI), lipofectin, lipofectamine, polylysine, and alginate. In a preferred embodiment, the non-viral delivery vehicle is poly (ethylenimine). Examples of viral vectors include, but are not limited to, adenovirus, adeno-associated virus, lentivirus, and retrovirus.

The upstream regulatory element can be selected from the group consisting of an cyclooxygenase promoter, a tumor necrosis factor promoter, an interleukin-2 promoter, an interleukin-21 promoter, and an interleukin-23 promoter. These upstream regulatory elements can be activated by their corresponding proteins, molecules, enzymes. That is to say that when the upstream regulatory element is a cyclooxygenase promoter such as a cyclooxygenase-2 promoter, then the overexpression of the protein cyclooxygenase-2 in the cell, will result inactivation of the cyclooxygenase-2 promoter. Thus, the protein which activates the upstream regulatory element can be selected from the group consisting of cyclooxygenase-2, tumor necrosis factor, interleukin-2, interleukin-21, and interleukin-23.

In various embodiments, the apoptosis-inducing gene can be selected from the group consisting of Caspase-1, Caspase-2, Caspase-3, Caspase-4, Caspase-5, Caspase-6, Caspase-7, Caspase-8, Caspase-9, Caspase-10, Granzyme A, Granzyme B, Fas ligand, TRAIL and APO3L. In a preferred embodiment, the apoptosis-inducing gene can be Caspase 3, and/or Caspase 9. The cell overexpressing the protein is typically a diseased cell, such as a cancer cell, a tumor cell, or an inflammatory cell.

In another aspect, the invention pertains to a chimeric gene construct comprising a cylooxygenase-2 promoter operably linked to an apoptosis-inducing gene. The expression of the apoptosis-inducing gene is driven by the cylooxygenase-2 promoter, and the apoptosis-inducing gene is expressed in a cell that overexpresses cylooxygenase-2, such that selectively induced apoptosis occurs in the cell.

The chimeric gene construct can further comprise a delivery vehicle such as a non-viral delivery vehicle or a viral delivery vehicle. Examples of non-viral delivery vehicle include, but are not limited to, poly(ethylenimine) (PEI), lipofectin, lipofectamine, polylysine, and alginate. In a preferred embodiment, the non-viral delivery vehicle is poly (ethylenimine). Examples of viral vectors include, but are not limited to, adenovirus, adeno-associated virus, lentivirus, and retrovirus.

In various embodiments, the apoptosis-inducing gene driven by the COX-2 promoter can again be selected from the group consisting of Caspase-1, Caspase-2, Caspase-3, Caspase-4, Caspase-5, Caspase-6, Caspase-7, Caspase-8, Caspase-9, Caspase-10, Granzyme A, Granzyme B, Fas ligand, TRAIL and APO3L. In a preferred embodiment, the apoptosis-inducing gene an be Caspase 3, and/or Caspase 9. The cell overexpressing cylooxygenase-2 is typically a diseased cell such as a cancer cell, a tumor cell, or an inflammatory cell.

In another aspect, the invention pertains to methods of selectively inducing apoptosis in a cell by delivering a chimeric gene construct to a cell. The chimeric gene construct can comprise a cyclooxygenase-2 promoter operably linked to an apoptosis-inducing gene, and the expression of the apoptosis-inducing gene is driven by the cylooxygenase-2 promoter in a cell that overexpresses cyclooxygenase-2. The method further includes the step of expressing apoptosis-inducing gene in the cell that overexpresses cyclooxygenase-2, such that an apoptosis-inducing protein is produced in the cell. The apoptosis inducing protein modulates an apoptosis pathway to cause the cell that overexpresses cyclooxygenase-2 to undergo apoptosis, thereby selectively inducing cell death.

DETAILED DESCRIPTION

Figure 1A:
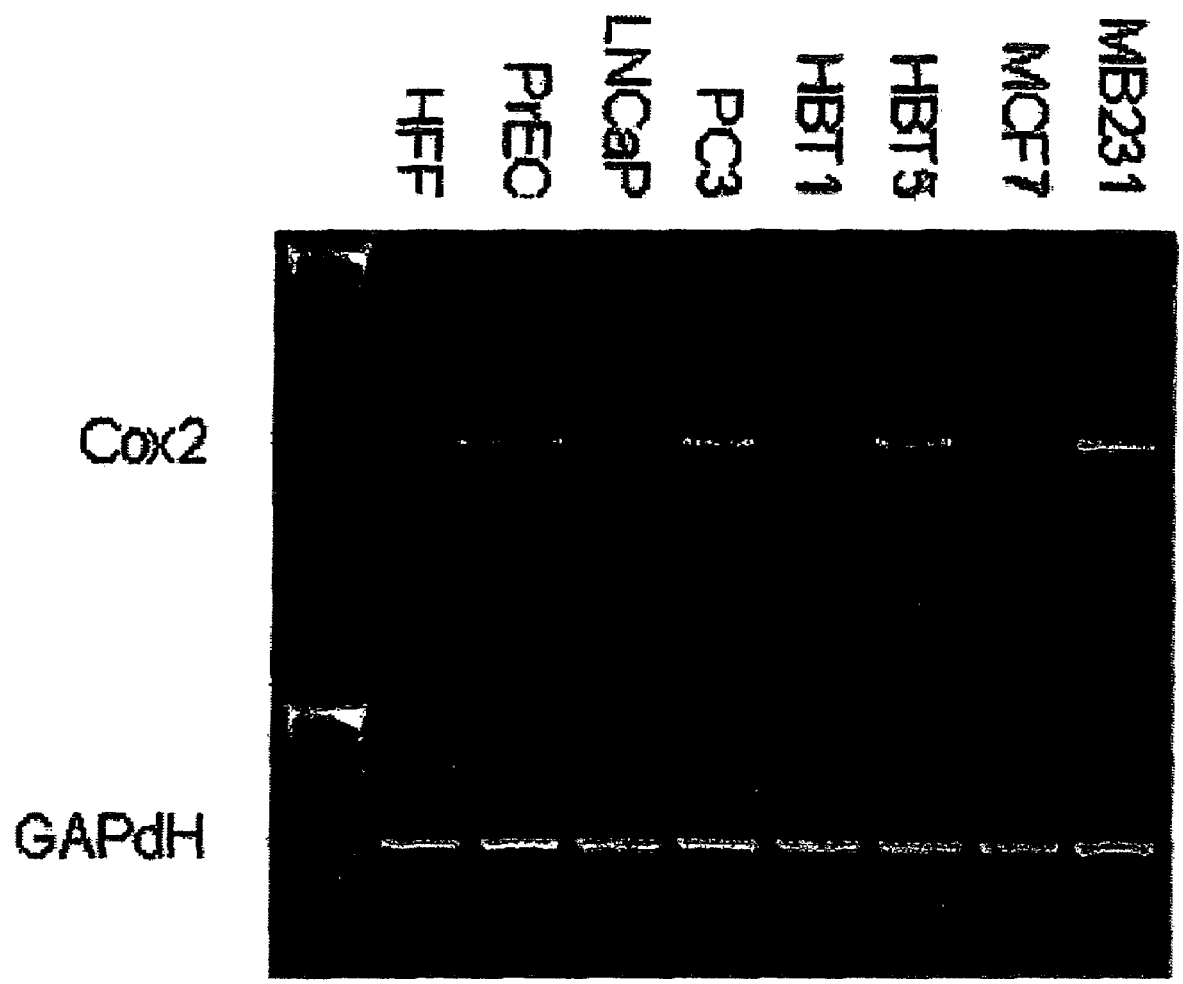
FIG. 1A is a photograph of a gel showing COX-2 transcription levels correlate with COX-2-driven expression of delivered genes.

The practice of the present invention employs, unless otherwise indicated, conventional methods of virology, microbiology, molecular biology and recombinant DNA techniques within the skill of the art. Such techniques are explained fully in the literature. (See, e.g., Sambrook, et al. Molecular Cloning: A Laboratory Manual (Current Edition); DNA Cloning: A Practical Approach, Vol. I & II (D. Glover, ed.); Oligonucleotide Synthesis (*N. Gait*, ed., Current Edition); Nucleic Acid Hybridization (*B. Hames & S. Higgins*, eds., Current Edition); Transcription and Translation (*B. Hames & S. Higgins*, eds., Current Edition); CRC Handbook of Parvoviruses, Vol. I & II (*P. Tijessen*, ed.); Fundamental Virology, 2nd Edition, Vol. I & II (*B. N. Fields and D. M. Knipe*, eds.))

So that the invention is more clearly understood, the following terms are defined:

The term "regulatory sequence", as used herein, includes promoters, enhancers and other expression control elements. Such regulatory sequences are known and discussed in Goeddel, Gene expression Technology: Methods in Enzymology, p. 185, Academic Press, San Diego, Calif. (1990).

The term "promoter" as used herein refers to a DNA sequence generally described as the 5' region of a gene, located proximal to the start codon. The transcription of an adjacent gene(s) is initiated at the promoter region. If a promoter is an inducible promoter, then the rate of transcription increases in response to an inducing agent. In contrast, the rate of transcription is not regulated by an inducing agent if the promoter is a constitutive promoter. The term "promoter" also includes fragments of a promoter that are functional in initiating transcription of the gene.

The term "expression" or "expressed" as used herein refers to is the process by which a polypeptide is produced from a structural gene. The process involves transcription of the gene into mRNA and the translation of such mRNA into polypeptide(s).

The term "cyclooxygenase-2" or "COX-2" refers to an inducible isoform of cyclo-oxygenase, a key enzyme in the conversion of arachidonic acid to prostaglandin. Expression of COX-2 is undetectable under physiological conditions but up-regulated at the transcriptional, post-transcriptional and protein levels in many cancers and tumors. COX-2, which is a PKC-dependent gene, is important for the genesis of cancer since its overexpression inhibits apoptosis and increases the invasiveness of tumor cells.

The phrase "COX-2 promoter" as used herein refers to an upstream regulatory element that controls transcription of an operably linked gene. The COX-2 promoter can contain a cAMP response element and sites for AP-2 and NF-kB that are both PKC-responsive cis-elements (Inoue et al. (1995) *J Biol Chem* 270:24965-71).

The phrase "promoter directed targeting" or "promoter based targeting" as used herein refers to selecting a specific population of cells that overexpresses COX-2, in which the elevated levels of COX-2 activate the COX-2 promoter. Activation of the COX-2 promoter results in transcription, translation and expression of the AIG. Selected populations of cells (i.e., those that overexpress, or have elevated levels of COX-2), can be targeted for destruction by using genetic transcription regulatory sequences (e.g., COX-2 promoter). This restricts the expression of the AIG to certain cell types, a strategy referred to as "promoter based targeting."

The phrase "apoptosis-inducing gene" or "AIP" as used herein refers to a gene that encodes a protein involved in the apoptotic pathway. Examples of apoptosis-inducing genes include, but are not limited to, members of the ICE/CED3 family of apoptosis inducing proteases (such as Caspase-1 (ICE), hICE, ICE-LAP45, Mch2 alpha), Caspase-2 (ICH1), Caspase-3 (CPP32, Yama, Apopain), Caspase-4 (TX, ICH2, ICE rel II), Caspase-5 (ICE rel III, TY), Caspase-6 (Mch-2), Caspase-7 (Mch-3, ICE-LAP3, CMH-1), Caspase-8 (MACH, FLICE, Mch-5), Caspase-9 (ICE-LAP6, Mch6) and Caspase-10 (Mch4)), members of the granzyme family (such as Granzyme A and Granzyme B), Fas ligand (FasL), and functional fragments, variants, and mixtures of any of these. Some embodiments employ Caspase 3, Caspase 4, Caspase 5, Granzyme B, and functional fragments, variants, and mixtures thereof. With the exception of FasL, these genes, when overexpressed following transfection, induce apoptosis in the transfected cells (Miura M., et al., (1993) *Cell* 75, 653-660; Chinnayan et al., (1995) *Cell*, 81, 505-512; Los, et al., (1995) *Nature* 375, 81; Muzio, et al., (1996) *Cell* 85, 817-827).

The term "apoptosis" as used herein refers to the art recognized use of the term for an active process of programmed cell death characterized by morphological changes in the cell. Apoptosis is characterized by membrane blebbing and nuclear DNA fragmentation.

The term "caspase" as used herein refers to a cysteine protease that specifically cleaves proteins after Asp residues. Caspases exist as inactive proenzymes which undergo proteolytic processing at conserved aspartic residues to produce 2 subunits, large and small, that dimerize to form the active enzyme. This protein was shown to cleave and activate caspases 6, 7 and 9, and itself could be processed by caspases 8, 9 and 10. Caspases are initially expressed as zymogens, in which a large subunit is N-terminal to a small subunit. Caspases are generally activated by cleavage at internal Asp residues. Caspases are found in a myriad of organisms, including human, mouse, insect (e.g., *Drosophila*), and other invertebrates (e.g., *C. elegans*). The caspases include, but are not limited to, Caspase-1 (also known as "ICE"), Caspase-2 (also known as "ICH-1"), Caspase-3 (also known as "CPP32," "Yama," "apopain"), Caspase-4 (also known as "ICE$_{-rellI}$"; "TX," "ICH-2"), Caspase-5 (also known as "ICE$_{-rellII}$"; "TY"), Caspase-6 (also known as "Mch2"), Caspase-7 (also known as "Mch3," "ICE-LAP3" "CMH-1"), Caspase-8 (also known as "FLICE;" "MACH;" "Mch5"), Caspase-9 (also known as "ICE-LAP6;" "Mch6"), Caspase-10 (also known as "Mch4," "FLICE-2"). The term "apoptosis-inducing gene" is also intended to include pro-forms of caspases, i.e., activatable intermediates in the apoptotic cascade. The caspases may be prepared inactive forms that require activation by an oligomerizing agent.

The phrase "oligomerizing agent" as used herein refers to a ligand that facilitates the association of a number of components to form dimers, trimers, tetramers, or oligomers. The oligomerizing agent can be used to associate like components, i.e., homodimerize. Alternatively, the oligomerizing agent can be used to associate different components, i.e, heterodimerize. The action of bringing the separate components together results in a triggering event that initiates cellular processes, such as apoptosis. For example, the oligomerizing agent can be a dimerizing agent such as AP20187 (Ariad), that facilitates the association of two caspases (e.g., caspase-3 and caspase 9), to trigger apoptosis in the cell. Accordingly, the oligomerizing agent provides an additional level of regulation in which apoptosis is activated when desired by administering the oligomerizing agent to the cell. Examples of oligomerizing agents include, but are not limited to, AP20187 (Ariad), FK-509-type ligands, cyclosporin A-type ligands, tetracycline, steroid ligands, the tetracycline Tet-On/Tet-Off system, an ecdysone-dimerizer system, an antiprogestin-dimerizer system, and the courmarin-dimerizer system. In one embodiment, the oligomerizing agent is AP20187 (Ariad). Examples of specific dimerizing agents include, but are not limited to, FKBP:FK1012, FKBP:synthetic divalent FKBP ligands, FRB:rapamycin/FKBP, cyclophilin:cyclosporin, DHFR:methotrexate, TetR:tetracycline or doxycycline or other analogs or mimics thereof, progesterone receptor:RU486, ecodysone receptor:ecdysone or muristerone A or other analogs or mimics thereof, and DNA gyrase:coumermycin.

The phrase "chimeric gene construct" as used herein refers to a genetic sequence composed of a regulatory element such as a promoter operably linked to an apoptosis-inducing gene, which can cause self-induced apoptosis selectively in a population of cells which have an elevated level of a protein associated with the promoter. For example, the chimeric gene construct can comprise a COX-2 promoter operably linked to an AIG. The chimeric gene construct induces apoptosis by expressing the AIG in those cells that have elevated levels of COX-2. Examples of cells with elevated levels of COX-2 include diseased cells, such as most cancer and tumor cells.

It is to be understood that although the chimeric gene construct may target any number of cells, the expression of the AIG will however, only occur in those cells in which the COX-2 promoter is activated to switch on expression of the AIG. Promoter activation will occur in those cells that have elevated levels of COX-2. For example, a chimeric gene construct comprising a COX-2 promoter and an AIG, can be used to target a mixed population of cells, some of which overexpress COX-2. Selective expression of the AIG will only occur in those cells that overexpress COX-2. Thus, the invention relies on cell specific promoter activation that results in a selected population of cells being destroyed without effecting cells that do not overexpress COX-2.

The phrase "self-induced apoptosis" as used herein refers to initiating the apoptotic process in a cell in which apoptosis has not occurred. The induction of apoptosis in the cell leads to a measurable increase of apoptotic activity in the cell. The increase in apoptotic activity can be determined by measuring parameters such as cell blebbing DNA fragmentation, and the like. The methods and constructs of the invention can force a cell to undergo apoptosis. For example, cells that overexpress COX-2, such as cancer cells, become resistant to apoptosis. However, the methods of the invention can actually use the overexpression of COX-2 to activate the COX-2 promoter and switch on expression of an AIG, thereby inducing apoptosis is a cell that was once resistant to apoptosis.

The terms "modifies," "modified," and "modulate" are used interchangeably herein and refer to the up-regulation or down-regulation of a pathway in a cell (e.g., the apoptotic pathway), the activation of the suppression of a pathway in a cell, or the increase, decrease, elevation, or depression of a protein, peptide, or secondary messenger involved in a pathway of a cell.

The term "subject" as used herein refers to any living organism in which an immune response is elicited. The term subject includes, but is not limited to, humans, nonhuman primates such as chimpanzees and other apes and monkey species; farm animals such as cattle, sheep, pigs, goats and horses; domestic mammals such as dogs and cats; laboratory animals including rodents such as mice, rats and guinea pigs, and the like. The term does not denote a particular age or sex. Thus, adult and newborn subjects, as well as fetuses, whether male or female, are intended to be covered.

The phrase "a disorder associated with COX-2 activity" or "a disease associated with COX-2 activity" as used herein refers to any disease state associated with the expression of COX-2. Examples of diseases include, but are not limited to, cancers or tumors of the bladder, breast, prostate, colon, rectal, esophagus, pancreas, kidney, gastrointestinals, ovaries, etc, as well as mesothelioma.

The term "inflammatory disorder" used herein refers to disorder that relates to a response to a tissue injury caused by pathogenic microorganisms, trauma, chemicals, toxins, heat, or immune defenses (i.e. autoimmune diseases) involving secretion of several mediators from the injured tissue and induction of immunocytes. When tissue cells are damaged or destroyed, acids and chemical mediators (i.e. cytokines, histamine, bradykinin, serotonin, etc.) get released resulting in the dilation and increased permeability of blood capillaries. The inflammatory reaction can occur locally or become systemic. In addition, inflammatory disorders comprise autoimmune disorders which are diseases caused by the body producing an immune response against its own tissues. Autoimmune disorders can be classified into two groups: systemic, causing damage to many organs, and localized, where only a single organ or tissue is directly damaged. The invention can be used to treat, for example, urinary tract infections (UTI) which produce an inflammatory response as a result of urinary tract cells harboring bacteria. In such instances, the constructs and methods of the invention can be used to target those cells that harbor the bacteria because the inflammatory response in such cells will be high. The chimeric construct may have an inflammatory promoter that is operatively linked to an AIG, for example, an IL-2 promoter operatively linked with a granzyme B exon. Other examples of inflammatory disorders that can be treated include, but are not limited to, rheumatoid arthritis, inflammatory bowel disease, cirrhosis, multiple sclerosis, chronic liver disease, ulcerative colitis, cell proliferative disorders, cancers, and inflammation associated with Alzheimer's Disease and stroke.

The term "inflammatory molecule" as used herein refers to a molecule that has been implicated in an inflammatory response. Examples of inflammatory molecules include classes of molecules involved in the prostaglandin pathway. Examples include, but are not limited to, $PGH_2$, $PGE_2$, $PGD_2$, $PGF_2a$ and $PGI_2$; molecules involved in the nitric oxide pathway, such as NO, iNOS, eNOS, cNOS; enzymes involved in the metabolism of arachidonic acid, such as COX-2 and COX-1, and derivatives thereof; members of the TNF Ligand Family, such as TNF-β, TNF-α, TNFSF4, TNFSF5, TNFSF6, TNFSF7, TNFSF8, TNFSF9, TNFSF10), TNFSF 11, TNFSF12, TNFSF13, TNFSF14; members of the Interleukin Family cytokines, including all interleukins from IL-1 though IL-40, and in particular, IL-2, IL-21, and IL-23.

The term "host" as used herein refers to any prokaryotic or eucaryotic cell that is the recipient of a chimeric gene construct. For examples of such hosts, see Sambrook et al., Molecular Cloning: A Laboratory Manual, Second Edition, Cold Spring Harbor Laboratory, Cold Spring Harbor, N.Y. (1989).

The phrase "a cell overexpressing COX-2" refers to a diseased cell with an elevated level of COX-2 compared with a normal cell of the same morphology and type. Examples of diseased cells that overexpress COX-2 include, but are not limited to, cancer cells, tumor cells, inflammatory cells, and the like.

The phrase "diseased cell" as used herein refers to a cell in a general population of cells that is unhealthy or harmful (e.g., a cancer or tumor cell) and requires elimination, destruction, or termination from the population of cells, thereby leaving a general population of cells without the diseased cell.

The invention is described in more detail in the following subsections:

I. Apoptosis

Apoptosis is characterized by a series of stereotype morphological features such as chromatin condensation, nuclear fragmentation, and the appearance of membrane-enclosed apoptotic bodies. These morphological changes are executed by aspartate-specific cysteine proteases (caspases) which can be activated by various apoptogenic signals.

Caspases belong to cysteine proteases family (Harvey et al. (1998) *Adv. Biochem. Eng. Biotechnol.* 62: 107-128) and share several common features such being homologous to interleukin-1-β-converting enzyme (ICE) (Alnemri et al. (1996) *Cell:* 87: 171), and containing a conserved pentapeptide active-site motif QACXG (SEQ ID NO: 1) (where X is R, Z or G) (Cohen et al. (1997) *Biochem J,* 3261-16). Caspases are synthesized as inactive proenzymes comprising an N-terminal peptide (Prodomain) together with one large and one small subunit. There are various types of caspases. The Initiator (Activator) caspases are the first to be activated on commitment of a cell to die. The initiator caspases cleave and activate effector (Executioner) caspases. The Executioner caspases cleave and activate cellular substrates. In addition, cytokine processors such as cytochrome C may also be involved.

The active caspase enzyme is a heterotetramer, containing two small and two large subunits. Activation of caspases during apoptosis results in the cleavage of critical cellular substrates, including poly(ADP-ribose) polymerase and lamins, so precipitating the dramatic morphological changes of apoptosis (Cohen, (1997) *Biochem. J.* 326:1-16). The initiator caspases carry long prodomain, and can process and activate their own and other inactive caspase zymogens when triggered by a death signal (Femandes-Alnerni et al. (1996) *Proc Natl Acad Sci USA;* 93: 7464-7469; Srinivasula et al. (1996) *Proc. Natl Acad Sci USA* 93: 14486-14491), whereas the executioner caspases do not (Huang et al. (2001) *Biochem Biophys Res. Commun;* 283: 762-769; Seol et al. (1999) *J Biol Chem:* 274: 2072-2076; Meergans et al. (2000) *Biochem J.* 349: 135-140). The executioner caspases such as caspases-3, remain dormant until the initiator caspases activate them by direct proteolysis (Li et al. (1997) *Cell* 91: 479-489).

When triggered by a death signal, the initiator caspases are recruited through their long prodomain by specialized adaptor molecules to form the death-inducing signaling complex (DISC) or APAF. Because of the trimeric nature of the DISC, three caspase molecules are brought into close proximity and activate the initiator caspases (Yang et al. (1998) *Mol Cell;* 1: 319-325; Muzio et al. (1998) *J Biol Chem;* 273: 2926-2930). When activated, the initiator caspase can activate itself and other inactive caspase zymogens including executioner caspases that are activated by direct proteolysis. The activated executioners then rapidly dismantle important cellular components, leading to the typical changes observed in cell apoptosis (Nicholson et al. (1997) *Trends Biochem Sci;* 22: 299-306; Salvesen et al. (1997) *Cell;* 91: 443-446; Meller et al. (2002) *Neurosci Lett;* 324: 33-36).

The initiator caspases appear to display some specificity according to the type of apoptotic signal. Two main activation cascades for apoptosis induction have been described (Sun et al. (1999) *J. Biol. Chem.* 274: 5053-5060; Earnshaw et al. (1999) *Annu. Rev. Biochem.* 68: 383-424; and Budihardjo et al. (1999) *Annu. Rev. Cell Dev. Biol.* 15: 269-290). Fas receptor-ligand interactions use caspase-8 activation to trigger the downstream executioner caspases. An alter-native mitochondrial pathway, which is triggered by various anticancer agents, involves activation of caspase-9 upon recruitment to the mitochondria by cytochrome C and apoptosis protease activation factor-1 (APAF-1).

More downstream, the initiator caspases lead to the activation of executioner caspases-3, -6, and -7, which in turn cleave specific proteins resulting in the typical hall-marks of apoptosis. Caspase-3 is specifically required for DNA fragmentation leading to the typical apoptotic pattern of DNA laddering.(Enari et al. (1998) *Nature* 391: 43-50; Liu et al. (1998) *Proc. Natl. Acad. Sci. USA* 95: 8461-8466). Caspase-3 is also necessary for other typical morphological features of apoptotic cell death (Janicke et al. (1998) *J. Biol. Chem.* 273: 9357-9360). Table 1 summarizes the various caspases that can be used in the methods of the invention. The nucleotide sequences encoding the caspases are available from Genbank.

TABLE 1

Summary of Various Caspases

| Class | Name | Regulatory unit | Adapter molecule | Optimal tetrapeptide |
|---|---|---|---|---|
| Activators | Caspase-2 | CARD | RAIDD | DXXD |
| | Caspase-8 | DED | FADD | (I/V/L)EXD |
| | Caspase-9 | CARD | Apaf-1 | (I/V/L)EHD |
| | Caspase-10 | DED | FADD | (I/V/L)EXD |
| Executioners | Caspase-3 | | | DEXD |
| | Caspase-6 | | | (I/V/L)EXD |
| | Caspase-7 | | | DEXD |
| Cytokine processors | Caspase-1 | CARD | CARDIAK | (W/Y/F)EHD |
| | Caspase-4 | CARD | | (W/Y/F)EHD |
| | Caspase-5 | | | (W/Y/F)EHD |
| | mCaspase-11 | | | |
| | mCaspase-12 | | | |
| | Caspase-13 | | | |
| | mCaspase-14 | | | |

CARD: Caspase recruitment domain
DED: Death effector domain

Other examples of AIGs that may be suitable in the invention are the apoptotic proteins of the BCL2 family. Members in this family include BAD, BAK1, BAX, BCL2, BCL2A1 (bfl-1), BCL2L1 (bcl-x), BCL2L11 (bim-like protein), BCL2L2 (bcl-w), BIK, BLK, BNIP3 (nip3), BOK (Mtd), HRK, MCL-1 (See e.g., Bak, Farrow et al., (1995), *Nature* 374:731; Chittenden et al., (1995) *Nature* 374:733; Kiefer et al., (1995), *Nature* 374:736), Bcl-X (Boise et al., (1993), *Cell* 74:597; Fang et al., (1994), *J. Immunol.* 153:4388), Bad (Yang et al., (1995), *Cell* 80:285), Bid (Wang et al., 1996), *Genes Develop.* 10:2859-2869), Bik (Bovd et al., (1995), *Oncogene* 11:1921-1928), Hrk (Inohara et al., (1997), *EMBO J.* 16:1686-1694) and Bok (Hsu et al., (1997), *Proc. Natl. Acad. Sci. USA* 94: 12401-12406)). The nucleotide sequences encoding these proteins are known in the art and available from Genbank.

Further examples of the methods and compositions of the invention include using an inflammatory promoter operably linked to an AIG to target cells that overexpress inflammatory molecules. The inflammatory promoter is activated by elevated levels of the inflammatory molecules that include, but are not limited to, members of the TNF Ligand Family, such as TNF-β, TNF-α, TNFSF4 (OX40 Ligand), TNFSF5 (CD40 Ligand), TNFSF6 (FasL), TNFSF7 (CD27 Ligand), TNFSF8 (CD30 Ligand), TNFSF9 (4-1BB Ligand), TNFSF10 (TRAIL), TNFSF11 (TRANCE), TNFSF12 (Apo3L), TNFSF13 (APRIL), TNFSF14 (HVEM-L); members of the TNF Receptor Family, such as LTBR, TNFRSF1A (TNFR1), TNFRSF1B (TNFR2), TNFRSF4 (OX40), TNFRSF5 (CD40), TNFRSF6 (Fas), TNFRSF7 (CD27), TNFRSF8 (CD30), TNFRSF9 (4-1BB), TNFRSF10A (DR4), TNFRSF10B (DR5), TNFRSF10C (DcR1), TNFRSF10D (DcR2), TNFRSF12 (DR3), TNFRSF14 (HVEM); members of the IAP Family such as BIRC1 (NIAP), BIRC2 (IAP2), BIRC3 (IAP1), BIRC4 (XIAP), BIRC5 (Survivin), BIRC6 (Bruce); TRAF Family: TANK (I-TRAF), TRAF1, TRAF2, TRAF3 (CRAF1), TRAF4, TRAF5, TRAF6, TRIP. Members of the CARD Family such as APAF1, ASC, BCL10 (HuE10), NOD1 (CARD4), NOL3 (Nop30), RIPK2 (CARDIAC); members of the Death Domain Family, such as CRADD, DAPK2, FADD, MYD88, RIPK1;embers of the Death Effector Domain Family such as CASP8AP2 (FLASH), CFLAR (CASPER), FADD, LOC51283 (BAR); members of the CIDE Domain Family such as CIDEA, CIDEB, DFFA, DFFB; and members of the p53 and ATM Pathway: ATM, CHEK1 (chk1), CHEK2

(chk2, Rad53), GADD45A, MDM2, P63, RPA3, TP53 (p53) (See e.g., Green, (2000) *Cell* 102: 1-4; Salvesen et al. (1999) *Proc. Nalt. Acad. Sci.* 96:10964-7; Nagata (1999) *Annu Rev Genet* 33:29-55; Budihardjo et al. (1999) *Annu Rev Cell Dev Biol* 15:269-90; Ekert et al. (1999) *Cell Death Differ* 6: 1081-6; Lutz (2000) *Biochem Soc Trans* 28 (2): 51-6; Inoue et al. (2000) *Exp Cell Res* 254 (1): 14-24; Deveraux et al. (1999) *J Clin Immunol* 19: 388-98; Orlinick et al. (1998) *Cell Signal* 10:543-51; Schulze-Osthoff et al. (1998) *Eur J Biochem* 254 (3): 439-59; and Singh et al. (1998) *J Interferon Cytokine Res* 18 (7): 439-50). The Interleukin Family cytokines, including IL-1 though IL-40, and in particular, IL-2, IL-21, and IL-23. The nucleotide sequences encoding these proteins are known in the art and available from Genbank.

Other proteins that have been identified as factors required for mediating activity of proteins, mainly caspases, involved in the apoptosis pathway, are cytochrome C (Lin et al., (1996) *Cell* 86:147-157), designed as Apaf-2. In addition to cytochrome C, the activation of caspase-3 requires two other cytosolic factors-Apaf-1 and Apaf-3. Apaf-1 is a protein homologous to *C. elegans* CED-4, and Apaf-3 was identified as a member of the caspase family, caspase-9. Both factors bind to each other via their respective NH2-terminal CED-3 homologous domains, in the presence of cytochrome C, an event that leads to caspase-9 activation. Activated caspase-9 in turn cleaves and activates caspase-3 (Liu et al., (1996) *Cell* 86:147-157; Zou et al., (1997) *Cell* 90:405-413; Li et al., (1997), *Cell* 91:479-489). Another protein involved in the apoptotic pathway is DNA fragmentation factor (DFF), a heterodimer of 45 and 40 kD subunits that functions downstream of caspase-3 to trigger fragmentation of genomic DNA into nucleosomal segments (Liu et al., (1997), *Cell* 89:175-184).

The invention relates to using any AIG, such as caspases 1, 3, 9, or combinations thereof to induce apoptosis in a cell overexpressing COX-2. In one embodiment, cell killing for example by apoptosis can be induced in a cell by expressing at least one AIG in a inactive, inducible form that is activated by an oligomerizing agent. The oligomerizing agent can be used to combine different inactive proteins, or subunits, to form an active protein. Examples of an oligomerizing agent include a dimerization agent that combines two subunits together, such as AP20187 (Ariad, Cambridge, Mass.). Other examples of specific dimerizing agents include, but are not limited to, FKBP:FK1012, FKBP:synthetic divalent FKBP ligands (see WO 96/0609 and WO 97/31898), FRB:rapamycin/FKBP (See e.g., WO 96/41865 and Rivera et al, (1997) *Nature Medicine* 2:1028-1032), cyclophilin:cyclosporin (See e.g. WO 94/18317), DHFR:methotrexate (See e.g. Licitra et al, (1996), *Proc. Natl. Acad. Sci. U.S.A.* 93:12817-12821), TetR:tetracycline or doxycycline or other analogs or mimics thereof (Gossen and Bujard, (1992), *Proc. Natl. Acad. Sci. U.S.A.* 89:5547; Gossen et al, (1995), *Science* 268:1766-1769; Kistner et al, (1996), *Proc. Natl. Acad. Sci. US.A.* 93:10933-10938), progesterone receptor:RU486 (Wang et al, (1994), *Proc. Natl. Acad. Sci. U.S.A.* 91:8180-8184), ecodysone receptor:ecdysone or muristerone A or other analogs or mimics thereof (No et al. (1996), *Proc. Natl. Acad. Sci. U.S.A.* 93:3346-3351, and U.S. Pat. No. 6,117,680) DNA gyrase: coumermycin (See e.g. Farrar et al. (1996), *Nature* 383:178-181), and antiprogestin. The oligomerizing agent may also be a trimerizing agent, that combines three subunits together, or a tetramizing agent that combines four subunits together, and the like. The oligomerizing agent may be administered systemically, e.g. by intravenous injection, or, locally to the target cell, e.g., a tumor cells. In a preferred embodiment, the caspases can be activated by administering an dimerizing agent, such as AP20187. The concentration of the dimerizing agent (e.g., for in vivo use will depend on the type of tissue being treated and the size of the subject. A suitable concentration of the dimerizing agents is in the range of about 0.1-20 mg/kg, preferably about 1-10 mg/kg, and more preferably about 2-5 mg/kg.

In another embodiment, apoptosis can be induced in a cell by expressing at least one AIG in an active form that initiates the apoptotic pathway without the need of an oligomerizing or activating agent. In this embodiment, the AIG's described above, e.g., caspases, can be used as non-inducible active forms in the chimeric constructs of the invention, whereby the expression of the caspase initiates the apoptotic pathway. For example, co-expression of caspase-9 and caspase-3 can activate the apoptotic pathway without requiring an oligomerizing agent such as AP20187. Also within the scope of the invention are chimeric constructs comprising nucleic acids that encode a fragment of an AIG, e.g., an active fragment of the AIG, a fragment corresponding to the small subunit, or the large subunit.

II. Promoter Based Targeting

In one aspect, the invention pertains to a method of selectively inducing apoptosis in a cell delivering a chimeric gene construct to a cell. The chimeric gene construct comprises an upstream regulatory element operably linked an apoptosis-inducing gene, and the expression of the apoptosis-inducing gene is driven by the upstream regulatory element in a cell that overexpresses a protein which activates the upstream regulatory element. The apoptosis-inducing gene is expressed the in the cell such that an apoptosis-inducing protein is produced in the cell. The apoptosis inducing protein modulates an apoptotic pathway to cause the cell to undergo apoptosis, thereby selectively inducing apoptosis in the cell.

In one embodiment, the invention is directed to selectively inducing apoptosis in a population of cells that overexpresses, or has elevated levels of a protein (COX-2) that can activate a promoter which corresponds to the overexpressed protein (COX-2 promoter). The activation of the promoter initiates transcription and expression of an AIG operably linked with the promoter. This is the principle behind promoter-based gene targeting which relies on activating a distinct promoter or enhancer that controls the gene for the given protein. If this upstream binding element is active within a population of cells, e.g., tumor cells, then plasmids that contain the same element can be engineered for expression in such cells. The overexpression of any protein can be utilized to target a given cell type. The expression of a protein can often be traced back to the transcriptional level. Thus, while several cell types might endocytose the chimeric gene constructs and translocate the delivered constructs into their nuclei, if the delivered AIG is under the control of a promoter that is utilized by only one cell type, then transcription of the AIG will only occur within that cell type and induce apoptosis in only these cells.

Thus, the methods and constructs of the invention selectively express an AIG in a population of cells that overexpresses COX-2. This population of cells can activate the COX-2 promoter that is operably linked to an AIG. The activation of the promoter in these cells leads to expression of the AIG and results in apoptosis and destruction of the cell without affecting cells that do not overexpress or have elevated levels of COX-2. The method and constructs of the invention can be used to target any cell that overexpress COX-2 to selectively purge these cells from a mixed population of cells.

The constitutive overexpression of COX-2 is a phenotypic behavior present in many cancer cells. This constitutive overexpression of cyclooxygenase 2 (COX-2), is linked with cellular resistance to senescence and therefore resistance to apoptosis, a hallmark of several cancerous cells (Watson (1998) *Histol Histopathol.* 13: 591-597). Constitutive COX-2 overexpression is also implicated as a component of tumorigenesis. COX-2 is an inducible component in the prostaglandin synthesis cascade, and is inducible in normal cells by many cytokines, mitogens, and pro-inflammatory factors. However, in the absence of these signals, normal cells do not express COX-2. This fact makes the COX-2 promoter a desirable candidate for targeting tumor cells at the transcriptional level.

The classes of cancers that demonstrate common COX-2 expression characteristics include, but are not limited to, many carcinomas, including those of intestinal epithelia (DuBois et al. (1996) *Cancer Res.* 56: 733-737), esophageal squamous cells (Shamma et al. (2000) *Clin Cancer Res.* 6:1229-1238), pancreatic cells (Molina et al. (1999) *Cancer Res.* 59: 4356-4362), various colorectal tumors (Watson et al. (1998) *Histol Histopathol.* 13: 591-597), adenocarcinoma (Battu et al. (1998) *Anticancer Res.* 18: 3579-3583), plus specific mammary (Subbaramaiah et al. (1996) *Cancer Res.* 56:4424-4429), prostate (Kamijo et al. (2001) *Int J Urol.* 8: S35-S39), prostate (Dempke et al. *J. Cancer Res. Clin. Oncol.* 127: 411-417 (2001), and bladder (Bostrom et al. (2001) *Pathology* 33: 469-474.) cancers. Although COX-2 is an inducible gene in untransformed cells, it is not normally expressed in healthy, unstressed tissues, including breast (Hwang et al. (1998) *J Natl Cancer Inst.* 90: 455-460.), prostate (Kamijo et al. (2001) Supra) and bladder (Yoshimura et al. (2001) *J Urol.* 165:1468-1472). This makes the COX-2 promoter suitable for cancer cell-targeted gene delivery.

III. Chimeric Gene Constructs

In one aspect, the invention pertains to a chimeric gene construct comprising an upstream regulatory element operably linked to a nucleic acid encoding least one AIG. The expression of the apoptosis-inducing gene is driven by the upstream regulatory element, and the apoptosis-inducing gene is expressed in a cell that overexpresses a protein which activates the upstream regulatory element, such that self-induced apoptosis occurs in the cell. The chimeric gene constructs of the invention are produced using standard recombinant molecular biology techniques as described by Sambrook et al., Supra. The AIG is under the transcriptional control of the upstream regulatory element which directs the expression of the AIG nucleic acid in a cell that overexpresses a protein which activates the upstream regulatory element In a preferred embodiment, the upstream regulatory element is the COX-2 promoter. The sequence of the human cyclooxygenase-2 gene is described in Kosaka, et al., (1994) *Eur. J. Biochem.* 221, 889-897. The region of human cyclooxygenase-2 gene constituting the promoter region may contain, for example, 1475 bases 5' of the cyclooxygenase-2 transcription start site having, for example, the sequence −1475/+59, or 1432 bases 5' of the cyclooxygenase-2 transcription start site having, for example, the sequence −1432/+59 or 375 bases 5' of the cyclooxygenase-2 transcription start site having, for example, the sequence −375/+59, or 327 bases 5' of the cyclooxygenase-2 transcription start site having, for example, the sequence −327/+59. Also within the scope of the invention are equivalents of the cyclooxygenase-2 gene, e.g., synthetic equivalent thereof, or other transcriptional promoter element of the human cyclooxygenase-2 gene operably linked to at least one AIG.

The various AIG that can be operably linked to the COX-2 promoter include those AIG's described under section II. The chimeric gene constructs can be prepared by ligating transcriptional promoter elements to the AIG by methods well-known in the art, e.g., by utilizing restriction enzymes to cut the reporter gene in appropriate portion to provide binding sites for the transcriptional promoter elements, incubating the restriction enzyme treated reporter gene with the transcriptional promoter elements and screening for the recombinants (See e.g, Sambrook et al., Supra).

Also within the scope of the invention are chimeric gene constructs with more than one upstream regulatory element, as long as at least one of the upstream regulatory elements is activated and capable of initiating transcription of the AIG. In other embodiments of the invention, at least two chimeric gene constructs can be used, whereby the first chimeric gene construct comprises an upstream regulatory element (e.g., COX-2 promoter) operably linked to a first AIG (e.g., Caspase 3), and the second chimeric gene construct comprises an upstream regulatory element (e.g., COX-2 promoter) operably linked to a second AIG (e.g., Caspase 9). In this embodiment, the activation of the COX-2 promoter in a cell that overexpressed COX-2 would lead to the expression of caspase-3 and caspase-9 in the cell and activate apoptosis.

In another embodiment, the chimeric gene constructs comprises different upstream regulatory elements, for example the first chimeric gene construct comprises a COX-2 promoter operably linked with a first AIG, while the second chimeric gene construct comprises an upstream regulatory element that is different from the COX-2 promoter (e.g., a IL-2 promoter), that is operably linked to a second AIG that is the same or different from the first AIG. In this embodiment, the activation of the COX-2 promoter in a cells that overexpressed COX-2 and the activation of IL-2 promoter is a cell that overexpressed IL-2, would lead to expression of the operably linked AIG's and activation of apoptosis in the cells. It is to be understood that a single cell population may have elevated levels of for example, COX-2 and IL-2, thereby activating apoptosis in a single cell population. Alternatively, apoptosis may be induced in different cell populations, one that has elevated levels of COX-2, and another than has elevated levels of IL-2.

Examples of other elevated proteins in cells that can be used to selectively induce apoptosis include, but are not limited to, IL-2, IL-21, IL-23. The corresponding promoters that can be used include, but are not limited to, IL-2, IL-21, IL-23.

In yet another embodiment, a population of cells that do not typically exhibit elevated levels of COX-2 may be targeted by first delivering a construct carrying the COX-2 gene into the cell and expressing the COX-2 protein in the cells. Such constructs can be prepared using standard recombinant molecular biology techniques. After overexpressing COX-2 in these cells, the cells can be targeted with the chimeric gene constructs of the invention to induce apoptosis in these cells.

IV. Delivery Systems

In one aspect, the invention pertains to delivering the chimeric gene construct to a cell. The chimeric gene construct can be delivered using a viral or a non-viral delivery system. Examples of non-viral delivery systems include, but are not limited to, poly(ethylenimine) (PEI), lipofectin, lipofectamine, polylysine, and alginate. In a preferred embodiment, the non-viral delivery system is the polycation, poly (ethylenimine).

The concept behind the majority of gene delivery targeting regimes involves the conjugation of ligands to gene delivery complexes. This idea was first used prior to gene delivery work with the attachment of ligands to liposomes for targeted delivery of drugs or proteins to specific cell types (Matthay et al. (1984) *Cancer Res.* 44: 1880-1886). However, problems still exist with ligand attachment methods in the in vivo setting due to possible recognition of ligands by immune cells or potential clearance in the liver due to either properties of the ligands themselves or the binding of serum proteins to ligands which mark the complexes for clearance. Partially in response to these complications, another form of targeted gene delivery has evolved that does not utilize cell-specific ligands; targeting is achieved at the transcriptional level through the use of upstream binding elements that are specific to certain cell types. Examples of using cell specific promoters for gene delivery targeting include dendritic (Langerhans) cells (Morita et al. (2001) *Gene Ther.* 8: 1729-1737), ovarian cells (Bao et al. (2002) *Gynecol Oncol.* 84: 228-234), and B-lymphoid cells (Maxwell et al. (1991) *Cancer Res.* 51: 4299-4304.), among others.

The Examples section includes results of the induction of apoptosis within cancer cells using a non-viral method to deliver caspase genes. The gene delivery vehicle selected for this work was poly(ethylenimine) (PEI), a polycation chosen for its branched structure to aid in DNA protection (Godbey et al. (2000) *J Biomed Mater Res.* 51: 321-218), as well as its potential for a high degree of protonation due to a high amine concentration within each molecule. Because of an abundance of primary amines within this polymer, the attachment of ligands or signaling molecules to PEI is not a chemical challenge. However, one goal of these investigations was to determine whether PEI can be used to deliver genes to cells in a targeted fashion without chemical modification. The PEI was conjugated to the chimeric gene construct and used to deliver the caspases to induce apoptosis in a cell. The ratio of PEI:DNA of about 1:1, 1.5.1, 2:1; 2.5:1, 3:1, 3.5:1, 4.1, 4.5:1; 6:1, 6.5:1, 7:1, 7.5:1, 8:1, 8.5:1, 9:1, 9.5:1. 10:1. Preferably, the ratio of PEI:DNA is about 2.5:1.

Other polycationic proteins within the scope of the invention include, but are not limited to, histones and protamines or synthetic polymers like polylysine, polyarginine, polyomithine, DEAE dextran, polybrene, which are effective intracellular delivery agents. A polycation is a polymer containing a net positive charge, for example poly-L-lysine hydrobromide. The polycation can contain monomer units that are charge positive, charge neutral, or charge negative, however, the net charge of the polymer must be positive. A polycation also can mean a non-polymeric molecule that contains two or more positive charges. A polyanion is a polymer containing a net negative charge, for example polyglutamic acid. The polyanion can contain monomer units that are charge negative, charge neutral, or charge positive, however, the net charge on the polymer must be negative. A polyanion can also mean a non-polymeric molecule that contains two or more negative charges. The term polyion includes polycation, polyanion, zwitterionic polymers, and neutral polymers. The term zwitterionic refers to the product (salt) of the reaction between an acidic group and a basic group that are part of the same molecule. Salts are ionic compounds that dissociate into cations and anions when dissolved in solution. Salts increase the ionic strength of a solution, and consequently decrease interactions between nucleic acids with other cations.

Polycations provide the advantage of allowing attachment of DNA to the target cell surface. The polymer forms a cross-bridge between the polyanionic nucleic acids and the polyanionic surfaces of the cells. As a result the main mechanism of DNA translocation to the intracellular space might be non-specific adsorptive endocytosis which may be more effective then liquid endocytosis or receptor-mediated endocytosis. Furthermore, polycations are a very convenient linker for attaching specific receptors to DNA and as result, DNA-polycation complexes can be targeted to specific cell types.

Additionally, polycations protect DNA in complexes against nuclease degradation. This is important for both extra- and intracellular preservation of DNA. The endocytic step in the intracellular uptake of DNA-polycation complexes is suggested by results in which DNA expression is only obtained by incorporating a mild hypertonic lysis step (either glycerol or DMSO). Gene expression is also enabled or increased by preventing endosome acidification with $NH_4Cl$ or chloroquine. Polyethylenimine, which facilitates gene expression without additional treatments probably disrupts endosomal function itself. Disruption of endosomal function has also been accomplished by linking the polycation to endosomal-disruptive agents such as fusion peptides or adenoviruses.

In another embodiment, the chimeric gene construct can be delivered to the cells using vectors. Vectors useful for in vivo gene therapy have been previously described and include retroviral vectors, adenoviral vectors and adeno-associated viral vectors (See e.g. Rosenfeld (1992) *Cell* 68, 143-155; Anderson (1984) *Science* 226, 401-409; Friedman, (1989) *Science* 244, 1275-1281). In another embodiment, the chimeric gene construct can be delivered to tumor cells in vivo by direct injection of naked nucleic acid into tumor cells (See e.g. Acsadi et al., (1991) *Nature* 332, 815-818). A delivery apparatus is commercially available (BioRad).

In another embodiment, the chimeric gene construct can be delivered using direct in vivo electrotransfection (DIVE), as described in U.S. Pat. No. 6,519,492 (incorporated herein by reference). In this process, the target cell is perfused with a transfection solution. An exterior electrode is positioned so as to surround at least a portion of the target tissue. One or more interior electrodes are placed within the target tissue. The perfusion and the application of the interior and exterior electrodes may be performed in any particular order. After the perfusion and the positioning of the electrodes, both interior and exterior, an electric waveform is applied through the exterior electrode and the interior electrode to transfect the cells in the target tissue. The transfection solution can be physiological saline, phosphate buffered saline and mixtures thereof. The salt content of the transfection solution may be increased or decreased to change the effective propagation of the electric field. This change and adjustment in salt content is particularly useful in a hollow organ, such as a bladder, which is filled with the transfection solution during DIVE.

The DIVE procedure can be used for selectively transfecting a subsegment of the cells of a target tissue, which can be an organ, using direct in vivo electrotransfection. In the method, a subsegment of the target tissue is perfused with a transfection solution comprising a nucleic acid construct. An exterior electrode is positioned to surround at least a portion of said target tissue. One or more interior electrodes is placed within the target tissue. Then an electric waveform is applied through the exterior electrode and the interior electrode to cause the transfection of a subsegment of the target tissue. Transfection specificity is maintained because only cells in contact with the transfection solution are transfected. The exterior electrode may be positioned on the skin of the patient if the electric conduction is sufficient. Electric conduction may be facilitated by the application of a electroconductive gel between the exterior electrode and the skin. This method may be useful, for example, if it is only desired to transfect a subsegment of an organ. For example, the bladder lining may be selectively transfected.

V. Modulation of Cells By Induced Apoptosis

The chimeric gene construct of the invention can be used to induce apoptosis in vitro or in vivo in a cell that overexpresses a protein (e.g., COX-2, or IL-2) capable of activating an upstream regulatory element (e.g., COX-2 promoter, or IL-2 promoter). Any cell that overexpresses COX-2 (e.g., tumor or cancer cells, or inflammatory cells), can be modified with the chimeric gene construct of the invention. The chimeric construct of the invention expresses at least one AIG that induces apoptosis in the cell thereby modulating the cell. Apoptosis can also be induced in a cell that does not typically undergo apoptosis such as a cell that is resistant to apoptosis due to the high level of the COX-2 protein in the cell.

Examples of cells that can be modulated include, but are not limited to, many carcinomas, including but not limited to, those of intestinal epithelia (DuBois et al. (1996) *Cancer Res.* 56: 733-737), esophageal squamous cells (Shamma et al. (2000) *Clin Cancer Res.* 6: 1229-1238), pancreatic cells (Molina et al. (1999) *Cancer Res.* 59: 4356-4362), various colorectal tumors (Watson et al. (1998) *Histol Histopathol.* 13: 591-597), adenocarcinoma (Battu et al. (1998) *Anticancer Res.* 18: 3579-3583), plus specific mammary (Subbaramaiah et al. (1996) *Cancer Res.* 56:4424-4429), prostate (Kamijo et al. (2001) *Int J Urol.* 8: S35-S39), prostate (Dempke et al. *J. Cancer Res. Clin. Oncol.* 127: 411-417 (2001), and bladder (Bostrom et al. (2001) *Pathology* 33: 469-474.) cancers. Although COX-2 is an inducible gene in untransformed cells, it is not normally expressed in healthy, unstressed tissues, including breast (Hwang et al. (1998) *J Natl Cancer Inst.* 90: 455-460.), prostate (Kamijo et al. (2001) Supra) and bladder (Yoshimura et al. (2001) *J Urol.* 165: 1468-1472). This makes the COX-2 promoter suitable for cancer cell-targeted gene delivery.

In fact, any cell that overexpresses COX-2 can be targeted using the methods and constructs of the invention such as a solid tumor of an organ, e.g., a tumor of the bladder, lung, liver, breast, colon, bone, and the like. Malignancies of solid organs include carcinomas, sarcomas, melanomas and neuroblastomas are also within the scope of the invention. The tumor cells can also be blood-borne (i.e., dispersed) malignancy such as a lymphoma, a myeloma or a leukemia.

The method of the invention can be used to selectively induce apoptosis in any cells that overexpresses COX-2 (such as inflammatory cells) to thereby modulate any disorder associated with elevated COX-2 levels. Also within the scope of the invention is the selective induction of apoptosis in a cell population that has an elevated level of a protein other than COX-2 (e.g., IL-2), that can activate its corresponding promoter (IL-2 promoter), such that the corresponding promoter, which is operatively linked with at least one AIG, is activated resulting in transcription and expression of the AIG, and the subsequent induction of apoptosis in the cell. Thus, the methods and compositions of the invention specifically target, kill, eliminate, destroy, or terminate a diseased population of cells from general population of cells, thereby leaving a general population of cells without the diseased population of cells.

VI. Pharmaceutical Compositions

In one aspect, the invention pertains to compositions and formulations comprising the chimeric gene construct of the invention. The chimeric gene construct of the invention can be formulated in a form suitable for topical application. For example, as a lotion, aqueous or aqueous-alcoholic gels, vesicle dispersions or as simple or complex emulsions (O/W, W/O, O/W/O or W/O/W emulsions), liquid, semi-liquid or solid consistency, such as milks, creams, gels, cream-gels, pastes and sticks, and can optionally be packaged as an aerosol and can be in the form of mousses or sprays. The composition can also be in a sunscreen. These compositions are prepared according to the usual methods. The composition can be packaged in a suitable container to suit its viscosity and intended use by the consumer. For example, a lotion or cream can be packaged in a bottle or a roll-ball applicator, or a propellant-driven aerosol device or a container fitted with a pump suitable for finger operation. When the composition is a cream, it can simply be stored in a non-deformable bottle or squeeze container, such as a tube or a lidded jar. The composition may also be included in capsules such as those described in U.S. Pat. No. 5,063,507.

The chimeric gene construct can be administered as compositions by various known methods, such as by injection (subcutaneous, intravenous, etc.), oral administration, inhalation, transdermal application, or rectal administration. Depending on the route of administration, the composition may be coated with a material to protect the compound from the action of acids and other natural conditions which may inactivate the composition. The composition can further include an additional agent.

The composition may also be administered parenterally or intraperitoneally. Dispersions can also be prepared in glycerol, liquid polyethylene glycols, and mixtures thereof and in oils. Under ordinary conditions of storage and use, these preparations may contain a preservative to prevent the growth of microorganisms.

Pharmaceutical compositions suitable for injectable use include sterile aqueous solutions (where water soluble) or dispersions and sterile powders for the extemporaneous preparation of sterile injectable solutions or dispersion. In all cases, the composition must be sterile and must be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyetheylene glycol, and the like), suitable mixtures thereof, and vegetable oils. The proper fluidity can be maintained, for example, by the use of a coating such as licithin, by the maintenance of the required particle size in the case of dispersion and by the use of surfactants. Prevention of the action of microorganisms can be achieved by various antibacterial and antifungal agents. In many cases, it will be preferable to include isotonic agents, for example, sugars, polyalcohols such as manitol, sorbitol, sodium chloride in the composition. Prolonged absorption of the injectable compositions can be brought about by including in the composition an agent which delays absorption, for example, aluminum monostearate and gelatin.

The composition may be orally administered, for example, with an inert diluent or an assimilable edible carrier. The composition and other ingredients may also be enclosed in a hard or soft shell gelatin capsule, compressed into tablets, or incorporated directly into the subject's diet. For oral therapeutic administration, the composition may be incorporated with excipients and used in the form of ingestible tablets, buccal tablets, troches, capsules, elixirs, suspensions, syrups, wafers, and the like. The percentage of the compositions and preparations may, of course, be varied. The amount of active compound in such therapeutically useful compositions is such that a suitable dosage will be obtained.

The tablets, troches, pills, capsules and the like may also contain a binder, an excipient, a lubricant, or a sweetening agent. Various other materials may be present as coatings or to otherwise modify the physical form of the dosage unit. For instance, tablets, pills, or capsules may be coated with shellac, sugar or both. Of course, any material used in preparing any dosage unit form should be pharmaceutically pure and substantially non-toxic in the amounts employed. As used herein "pharmaceutically acceptable carrier" includes any solvents, dispersion media, coatings, antibacterial and antifungal agents, isotonic and absorption delaying agents, and the like. The use of such media and agents for pharmaceutically active substances is well known in the art. Except insofar as any conventional media or agent is incompatible with the active compound, use thereof in compositions of the invention is contemplated.

It is especially advantageous to formulate compositions of the invention in dosage unit form for ease of administration and uniformity of dosage. Dosage unit form as used herein refers to physically discrete units suited as unitary dosages for the subjects to be treated. Each dosage contains a predetermined quantity of active compound calculated to produce the desired therapeutic effect in association with the required pharmaceutical carrier. The specification for the novel dosage unit forms of the invention is dependent on the unique characteristics of the composition containing the antioxidant and the particular therapeutic effect to be achieved. Dosages are determined by reference to the usual dose and manner of administration of the ingredients.

In one embodiment, the dosage composition is selected to induce apoptosis in a cell as determined by measuring morphological parameters such as DNA fragmentation and cell blebbing. Alternatively, the dosage may be determined based on reduction in tumor size, for example by monitoring the size of the tumor by ultrasound as described in the Examples section.

The combinations of the invention may be used on their own, or preferably as a pharmaceutical composition in which the compounds or derivatives are in a mixture with a pharmaceutically acceptable adjuvant, diluent or carrier. For example in a form appropriate for enteral or parenteral administration. The pharmaceutical composition preferably comprises less than 80% and more preferably less than 50% of the compound or derivative. Examples of suitable adjuvants, diluents and carriers are well known to a person skilled in the art and include microcrystalline cellulose, calcium phosphate, diatomaceous earth, a sugar such as lactose, dextrose or mannitol, talc, stearic acid, starch, sodium bicarbonate and/or gelatin.

EXAMPLES

Example 1

Methods and Materials (A) Cells

Both normal and cancerous tissues were represented by a variety of cell types. Normal tissue was represented by prostate epithelial cells (PrEC) and human foreskin fibroblasts (HFF). Transformed cells were used to represent cancers of the prostate (PC3, LNCaP), bladder (HTB1, HTB5), and breast (MCF7).

| Abbrev. | Origin | Medium |
|---|---|---|
| PC3 | Prostate cancer | RPMI, 10% FBS, Penicilin/Streptomycin |
| LNCaP | Prostate cancer | RPMI, 10% FBS, Pen./Strep |
| HTB1 | Bladder cancer | DMEM, 10% FBS, Pen./Strep |
| HTB5 | Bladder cancer | DMEM, 10% FBS, Pen./Strep |
| MCF7 | Breast cancer | DMEM, 10% FBS, Pen./Strep |
| PrEC | Normal human prostate (Biowhittaker/Clonetics) | Prostate epithelium basal medium, supplemented with bovine pituitary extract, insulin, hydrocortisone, gentamycin, retinoic acid, transferrin, thyroid hormone T3, epinephrine, and human epidermal growth factor. (Clonetics #CC-3166) |
| HFF | Human foreskin fibroblasts | DMEM, 10% FBS, Pen./Strep |

(B) Plasmids

Engineered plasmids were manufactured using pEGFP-N1 (Clontech, Palo Alto, Calif.) as a starting vector. The existing $CMV_{ie}$ promoter was excised from pEGFP-N1 using AseI and BglII restriction enzymes, followed by blunt ending with the Klenow fragment and re-ligation using T4 ligase. The promoterless plasmid was then cut with XhoI and HindIII, followed by insertion of the human COX-2 promoter (−891 to +9) (courtesy of K. K. Wu, The University of Texas Health Science Center at Houston, Houston, Tex.) excised to contain sticky ends complementary to the plasmid being engineered (Tazawa et al. (1994) *Biochem Biophys Res Commun.* 203: 190-199). The resulting plasmid coded for an enhanced green fluorescent protein (GFP) under the control of the human COX-2 promoter.

Additional constructs were produced through modification of this reporter plasmid through replacement of the EGFP exon with the exon for inducible caspase 3 (iCasp3) or inducible caspase 9 (iCasp9) using SacII and BamHI restriction sites. Because of an existing BamHI site within the coding region of the caspase plasmids, partial digestion of the donated iCasp plasmids was required and achieved through the use of sub-optimal BamHI digestion conditions. Appropriately sized fragments were excised after agarose gel electrophoresis, and purified using a Gel Extraction Kit (Qiagen).

(C) Activation of Inducible Caspases

The proform caspases were made active through addition of AP21087, a component of the ARIAD homodimerization kit (ARIAD, Cambridge, Mass.). The molecule was delivered 2 days post-transfection at a concentration of 1.0 nM in growth medium.

(D) Analysis of Transcription

Transcription levels of COX-2 and the housekeeping gene GAPDH were analyzed via RT-PCR of total RNA. Cells were grown in 10 cm dishes to approximately 80% confluence, followed by scraping and RNA isolation via a commercially available kit (cat. #74104, Qiagen, Valencia, Calif.). COX-2 cDNA (304 bp) was amplified using the following primers: sense TTCAAATGAGATTGTGGGAAAATTGCT (SEQ ID NO: 2), antisense AGATCATCTCTGCCTGAGTATCTT (SEQ ID NO: 3). GAPDH cDNA was amplified using the following primers: sense TCACCATCTTCCAGGAGCG (SEQ ID NO: 4), antisense CTGCTTCACCACCTTCTTGA (SEQ ID NO: 5). RT-PCR was performed using 34 cycles of: denaturation at 95° C. for 1:30, annealing at 58° C. for 2:00, and extension at 73° C. for 0:40. The RT-PCR products were loaded onto a 1.5% agarose gel and run at 85 volts for approximately 1 hour. Photoimaging was performed with a Stratagene Eagle Eye II, and printed using Eagle Sight version 3.2 software. Densitometry was then performed using NIH Image 1.61 software.

(E) Transfection

Gene delivery was performed as previously published using the non-viral gene delivery vehicle PEI (Godbey et al. (1999) *Gene Ther.* 6: 1380-1388). Cells used for in vitro PEI-mediated transfections were plated at approximately $1.04 \times 10^4$ cells/cm$^2$ (100,000 cells per 35 mm dish) and allowed to grow approximately 16 hours prior to transfection. Specifications of the PEI-mediated transfections include a 7.5:1 PEI amine to DNA phosphate ratio based upon 3.6 µg of DNA per 35 mm plate transfection. The PEI used (Sigma-Aldrich, St. Louis, Mo., cat. #40,872-7) had a weight-average molecular weight ($M_w$) of approximately 25,000 Da. Transfections were allowed to proceed for 2 hours at 37° C. after which the transfection medium was aspirated and replaced by 2 ml of growth medium.

Analyses of transfection were performed either visually using an Olympus IX70 inverted microscope with an IXFLA fluorescence attachment, or via FACS using a FACScalibur (Becton Dickinson, San Jose, Calif.) set to a flow rate of 1 μl/sec with Cell Quest version 3.3 software. Transfection efficiencies for GFP-transfected cells are defined as the percentage of cells expressing GFP per total number of cells counted.

(F) Co-Culture Experiments

For certain cells to be used in co-culture experiments, the red fluorescent marker 5-(and-6)-chloromethyl SNARF®-1 acetate (cat. # C-6826, Molecular Probes, Eugene, Oreg.) was used to pre-label cultures. For a given pair of cell types, each was grown to late log stage in T-25 flasks. The cell type to be labeled was washed one time with PBS/EDTA, and incubated at 37° C. for 30 minutes in the appropriate serum-free medium containing 20 μM of the cell label. The staining medium was removed and the cells were washed once with PBS/EDTA followed by trypsinization for plating of the co-cultures. Co-cultures were carried out in 6-well plates with approximately 50,000 cells of each cell type (100,000 cells total) plated one day prior to transfection.

(G) DNA Fragmentation Analysis

ELISA was used to detect histone-bound DNA fragments. The Cell Death Detection ELISA$^{Plus}$ (Roche, Mannheim, Germany) kit employed anti-histone-biotin antibodies to bind the histone component of the nucleosomes from cell lysates to streptavidin-coated 96-well plates. Anti-DNA-POD was used to bind the developing agent to the DNA component of the bound nucleosomes. Cells were grown in 24-well polystyrene plates, and cell lysis was achieved by using 150 μl of the supplied lysis buffer per well, followed by incubation for 5 minutes at 37° C. All subsequent steps were performed according to the manufacturer's recommendations.

(H) Cytoskeletal Degradation Analysis

Immunofluorescence staining was used to detect cytoskeletal degradation, which is a marker of apoptosis. M30 CytoDEATH*, Fluorescein (Roche) is a fluorescein-conjugated mouse IgG specific to a caspase-cleaved epitope of the human cytokeratin 18 cytoskeletal protein. Following fixation in cold methanol for 1 hour at 4° C., cells (grown on a 24-well culture plate) were washed 2 times with phosphate-buffered saline (PBS) containing 0.1% Tween 20. The M30 CytoDEATH* antibody was diluted 1:120 in a solution of PBS containing 1.0% bovine serum albumin and 0.1% Tween 20, and 100 μl were added to each well of prepared cells. The reactions were allowed to proceed on a shaker in the dark for 1 hour at room temperature. Following the incubation, cells were mounted with one drop of Vectashield that contained DAPI (for labeling nuclei).

(I) Microscopy

All phase contrast and fluorescent cell images were captured using an Olympus IX70 inverted microscope and Magnafire imaging software.

(J) Statistics

Groups of data were analyzed by single-factor ANOVA. For pair-wise comparisons, the F-test was used to determine whether a given pair of population variances was equal ($\alpha$=0.05). This information was then used in designating the appropriate t-tests (typically heteroscedastic) to perform for comparing the means of population pairs. Significantly different pairs were defined as having p<0.05.

Example 2

COX-2 Overexpression in Tumor Cells

This example shows that cells overexpressing COX-2 can be used as targets. The initial stages of invention development were performed in vitro using human cells. A total of 8 cell types were used for demonstrating whether COX-2-overexpression could be used to target certain tumor types. The cells chosen originated from 1 of 2 groups: normal, untransformed cells or cancerous cells. The untransformed cells were either human foreskin fibroblasts (HFF) or prostate epithelial cells (PrEC). The types of carcinomas selected represent 3 affected tissues types—prostate (PC3 and LNCaP cell lines), bladder (HTB5 and HTB1), and breast (MB231 and MCF7)—and within these subgroups 2 cell lines, one that constitutively overexpresses COX-2 and one that does not, were investigated to verify the principle of expression targeting. The level of COX-2 expression in these cell types was verified by RT-PCR. FIG. 1A is a photograph of an agarose gel showing that COX-2 transcription levels correlate with COX-2-driven expression of delivered genes. Of the cell types examined, only PC3, HTB5, and MB231 overexpressed COX-2.

Figure 1B:
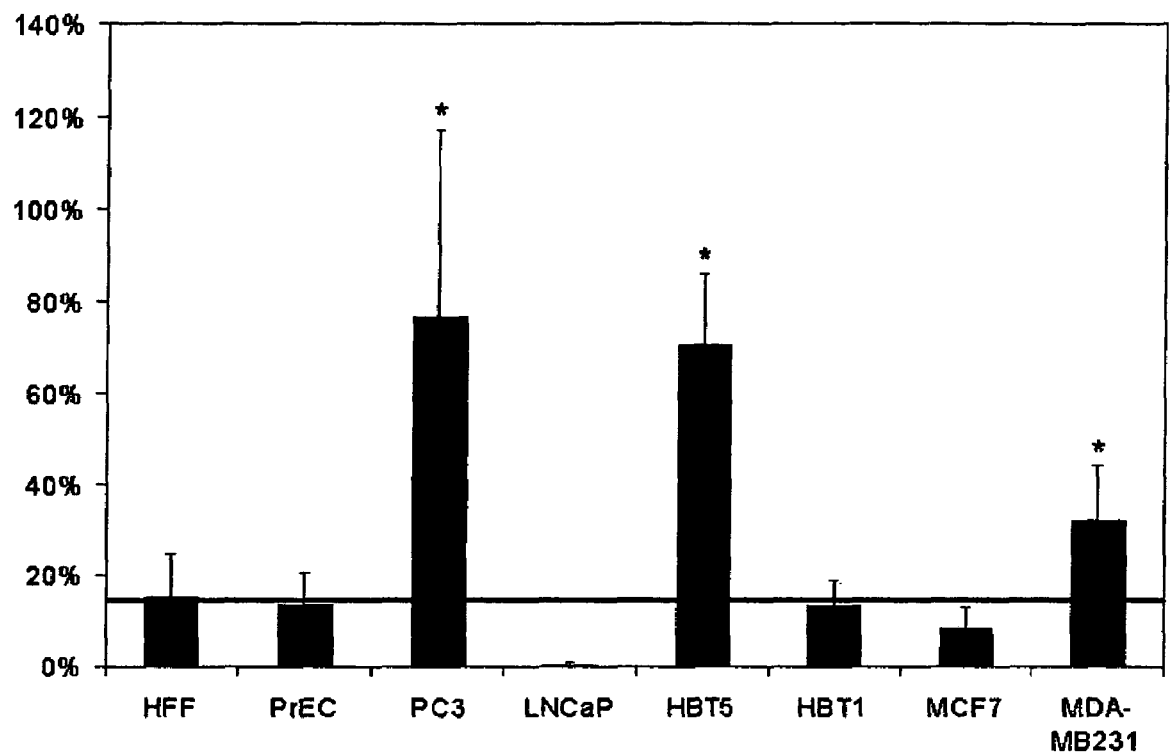
FIG. 1B is a bar chart depicting that only the three COX-2 overexpressing cell lines expressed the GFP reporter plasmid.

An enhanced green fluorescent protein (GFP) reporter gene driven by the human COX-2 promoter (COX2-GFP) was delivered to cells via the polycation PEI. The results showed that GFP expression was reduced by an average of 89.8% in normal cells and cell lines not overexpressing COX-2 when the strong CMV promoter was replaced with the human COX-2 promoter in delivered plasmids (not shown). Because the efficiency of gene transfer differs between cell types, transfection efficiencies for each cell type were normalized to their positive controls, where the delivered gene was the GFP gene driven by the strong promoter $CMV_{ie}$ (cytomegalovirus) (CMV-GFP). This normalization is expressed as a ratio of the transfection efficiencies of COX2-GFP to CMV-GFP, where transfection efficiency is defined as the percentage of cells expressing GFP out of the entire population. FIG. 1B is a bar chart depicting the normalized comparison of targeted versus untargeted transfections. When adjusted for the positive control (CMV-driven) transfection efficiency for each cell type, only the three Cox-2 overexpressing cell lines expressed the GFP reporter plasmid. *=Significantly different from the combined data sets for all non-Cox-2-overexpressing cells ($n^3 4$, p<0.05). Using this methodology, it was found that only the three COX-2-overexpressing cell lines—PC3, HTB5, and MB231—expressed GFP under the COX-2 promoter control system at levels significantly higher than untransformed control cells (FIG. 1B). The results clearly demonstrated that this gene therapy system can be used to target COX-2 overexpressing cells.

Example 3

Specific Targeting in Cells Overexpressing COX-2

Figure 2:
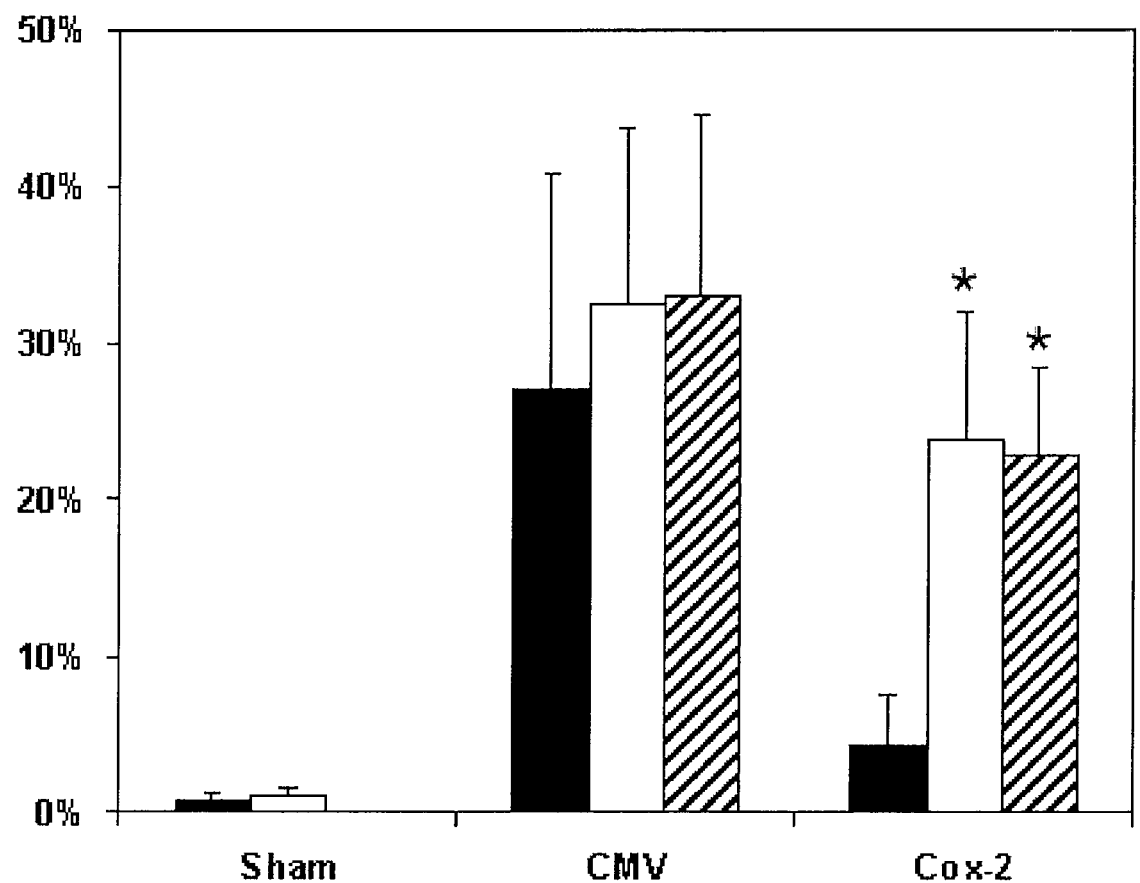
FIG. 2 is a bar chart depicting the percentage of cells in monoculture expressing GFP when transcription was directed by the CMV or the COX-2 promoter.

To further demonstrate the applicability of COX-2-driven gene expression for specific targeting of tumor cells, co-cultures of transformed and normal cells were grown and transfected with the COX2-GFP reporter. Construction of COX2-GFP constructs is described in Example 1(B). To help distinguish between the two cell types within the co-culture, a monoculture of one cell type was fluorescently labeled prior to combining it with a monoculture of a different cell type as described in Example 1(F). FIG. 2 is an example of this procedure, where untransformed HFF cells were labeled red before mixing them with a culture of immortal PC3 cells. After combining the two cell types to create an easily distinguishable co-culture, the cells were incubated overnight prior to transfection to facilitate gene delivery. Transfection results from delivery of the non-specific CMV-GFP control plasmid showed a roughly equivalent percentage of HFF and PC3 cells expressing the green reporter. (Red-labeled cells expressing the GFP reporter often showed up as yellow on computer-generated overlay images.) However, when the COX2-GFP plasmid was delivered to co-cultures, the untransformed cells failed to express the reporter in appreciable amounts. (The transfection efficiency of the untransformed cells using this system was less than 0.5%.) However, PC3 and HTB5 cells transfected in the HFF co-culture setups expressed the green fluorescent protein reporter at roughly 25-35% transfection efficiency in the COX2-driven systems.

Fibroblasts were labeled with red dye, PC3 cancer cells were unlabeled (Figure not shown). The co-culture cells were transfected with a GFP gene driven by one of 2 promoters. (A) Transfection with CMV-GFP plasmid in which both fibroblasts and PC3 cells express the GFP reporter. (B) Transfection with COX2-GFP plasmid in which only PC3 cells express the reporter. The transfection efficiency of COX-2-driven expression was <0.05% for fibroblasts in co-culture. F="Fibroblast," CA="Cancer cell,"+="Expresses reporter,"−="Not expressing reporter." FIG. 2 is a bar graph depicting the percentage of cells in monoculture expressing GFP when transcription was directed by the CMV or the COX2 promoter. CMV-driven transfection efficiencies were typically in the range of 25-35%. *=significantly different from HFF transfection efficiency ($n^3 6$, $p<0.00001$). The solid black bar=HFF cells, the white bar=PC3 cells, and the striped bar=HBT5 cells.

The results of such a transfection in an HFF/PC3 co-culture with red-labeled fibroblasts, wherein a lack of red-labeled cells expressing the green reporter is noted (data not shown). The converse experiment, which utilized red-labeled cancer cells and unlabeled fibroblasts, was also performed and produced similar transfection efficiencies (not shown). The data also shows the monoculture transfection efficiencies of these cell types when transfected with each of the two types of promoter-driven plasmids. These results demonstrated that healthy, unstressed, normal cells do not express COX-2 in sufficient amounts to be affected by this form of gene targeting.

The presence of limited COX-2 expression does not result in apoptosis in our system: RT-PCR data from FIG. 1 show that the normal cell types tested did express COX-2 to a limited extent in the experimental environments in which they were kept, but the transfection data show that this limited amount of COX-2 expression was not enough to yield reporter expression or apoptosis using the COX-2-driven transfection system.

Example 4

Construction of Functional Plasmids

Following the establishment of the expression targeting system for singling out COX-2-overexpressing cancer cells, COX2-driven plasmids were modified to code for a functional gene. Although the ultimate goal of these investigations is to destroy cancer cells, delivering a toxic protein that will result in tumor death via cell necrosis is undesirable because lethal proteins would be released from transfected cells following lysis. A bystander effect would result which would potentially kill healthy, untransformed cells in the area. It is for this reason that a gene product involved with apoptosis is a desirable candidate for bringing about cell death, and that caspases were selected as the functional product of our COX-2-targeted transfections, because apoptotic cells package their own degradation products to prevent a bystander effect.

Functional plasmids under the control of the COX-2 promoter were constructed as described in Example 1. These plasmids coded for modified forms of proteins involved with apoptosis. The basic proteins, caspases 3 and 9, are members of the apoptosis cascade, with caspase 9 being an initiator molecule and caspase 3 being an executioner molecule within the cascade (Huppertz et al. (1999) *Anat Embryol* (Berl). 200: 1-18). The modifications applied to these proteins resulted in pro-forms of the molecules that required homodimerization for their activation. The homodimerization was achieved through the addition of AP20187 (ARIAD, Cambridge, Mass.). The inducibility of the gene products gives an additional level of control to the gene delivery system at the post-translational level, a potentially important feature for when the system moves to an in vivo setting.

Example 5

In vitro Expression of Apoptosis-Inducing Genes

This Example demonstrates the in vitro effect of overexpressing apoptosis-inducing genes in cell-lines and activating the caspases with an oligomerizing agent. COX-2-overexpressing cells were transfected with COX2-iCasp3 plasmids as described in Example 1(E). Cells ((A) HTB5 cells an (B) PC3 cells) were transfected with a gene coding for inducible caspase 3 condensed following administration of the activator AP20187. The same was true for inducible caspase 9 (not shown).

The phase contrast images show that many COX-2-over-expressing cells transfected with the COX2-iCasp3 plasmids condensed within 8 hours after the addition of the AP20187 activator (data not shown). In addition, many cells within these cultures demonstrated a more granular cytoplasm, and there appeared to be a greater number of vesicular structures in the supernatants as compared to controls—transfected cells not receiving AP20187 and HFF cells (not shown). These findings were also seen in COX-2-iCasp9-transfected cells that received the AP20187 activator. These qualitative findings are consistent with apoptosis.

Example 6

Characterization of Apoptosis

On a molecular level, apoptosis is characterized, in part, by fragmentation of chromosomal DNA into nucleosomes. To show that the morphological changes seen in COX-2-overexpressing cells were due to apoptosis, ELISA was used to detect and quantify these histone-bound DNA fragments in HTB5 cells 8 hours after the addition of activator. $A_{405}$ results for all samples were normalized to those of sham transfections. CID=chemical inducer of dimerization (AP20187—activator of delivered caspases), iCasp3 mutant=inactive variation of inducible caspase 3, No prom=transfections that utilized a promoterless iCasp3 plasmid, *=significantly different from sham treated data ($p<0.05$), ###=no difference between groups (ANOVA, $p>0.775$).

Figure 3:
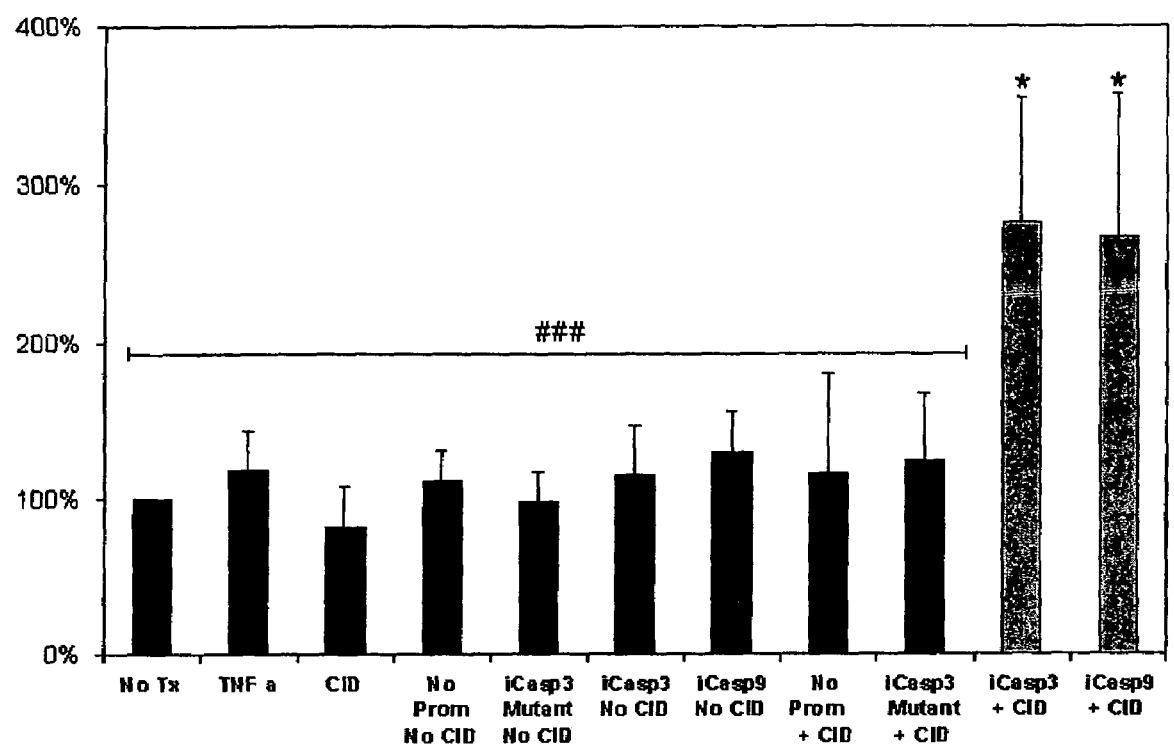
FIG. 3 is a bar chart depicting DNA fragmentation in response to caspase production and activation. DNA fragmentation was detected via ELISA against nucleosome-bound DNA.

This method also allowed for the distinction between apoptosis and necrosis, based on the fact that necrosis is characterized by rapid plasma membrane permeablization and would have been completed much sooner than 8 hours post-activation. Removing cell supernatants prior to the ELISA procedure removed any DNA fragments produced by necrotic processes. Results from these experiments demonstrate a significant increase (p<0.05) in the number of histone-bound DNA fragments 8 hours after the addition of AP20187 in COX2-iCasp3- and COX2-iCasp9-transfected cells (FIG. 3). ANOVA analysis of these data demonstrates no significant difference between groups for the set containing all controls plus iCasp transfections that did not also include the AP20187 activator (ANOVA, p>0.775), but that also including either of the iCasp+AP20187 data sets results in significant differences between groups (p<0.0005).

The existence of apoptosis was further confirmed at the molecular level through fluorescent immunostaining. Fluorescein-conjugated antibodies were used to label a specific cleavage site of cytokeratin 18 (CK18), an intermediate filament protein. Cells transfected with COX2-iCasp3 which also received the activator stained positively for cleaved CK18, while sham transfected cells and cells transfected with the COX2-iCasp3 plasmids but not receiving the activator did not stain for cleaved CK18 (data not shown). With cytoskeleton degradation being one of the results of apoptosis, the positive staining of cleaved CK18 seen in transfected cells supports the claim that the delivered, activated caspases cause apoptotic death in affected cells.

The data shows that the polycation PEI can be used to deliver genes into cells in a targeted fashion without modification of the polymer. It was also demonstrated that cells that constitutively overexpress COX-2 will readily transcribe delivered plasmids that are under the control of the COX-2 promoter. In addition, the results proved that inducible forms of both initiator and executioner caspases are effective in such a controlled system on a variety of tumor types, including those resistant to apoptosis due to a lack of certain receptors.

The polycation PEI was selected for transfection. Among non-viral gene delivery methods, PEI has been shown to yield relatively high transfection efficiencies, in part because PEI offers protection to the DNA it carries following endocytosis (Godbey et al. (2000) *J Biomed Mater Res.* 51: 321-218) as the delivered DNA is trafficked into cell nuclei (Godbey et al. (1999) *Proc Natl Acad Sci USA.* 96: 5177-5181). This is in contrast to liposomal methods, which deliver unprotected DNA into cell cytoplasms (Zelphati et al. (1996) *Proc Natl Acad Sci USA.* 93: 11493-11498). Although no mechanism for DNA release from PEI following endocytosis has yet been shown, there exists evidence that such release is not necessarily required for transcription of the delivered genes (Bieber et al. (2002) *J Control Release.* 82: 441).

As shown in FIGS. 1 and 2, COX-2-driven reporter expression was only seen in COX-2-overexpressing cells. Of note is the lack of expression in normal cells, especially in co-culture conditions. This specificity of expression serves as one component of the safety of a potential COX-2-driven treatment of cancer cells. In addition, COX-2 overexpression is thought to be one of the preliminary events in cell transformation (Shamma et al. (2000) supra; Howe et al. (2001) *Endocr Relat Cancer.* 8: 97-114), so this targeting method could also be useful as an early stage treatment, affecting pre-cancerous cells that might go otherwise undetected.

Example 7

In vivo Expression of Apoptosis Inducing Genes

This example describes the investigation of selective expression of apoptosis-inducing genes in vivo. Further invention development was performed in a mouse model. All plasmids were re-engineered to utilize murine control elements, using the mouse COX-2 promoter, TIS-10. Bladder tumors were implanted using MB49 cells with a technique described by Gunther et al. (See Gunther et al. (1999) *Cancer Res.* 59:2834-2837). Following 1 week of incubation to establish tumor tissue, treatments consisted of mouse bladder catheterization and instillation of the described gene therapy complexes.

Transfection solution volumes of approximately 66-75% of bladder capacity (100 μl were used in the tested mice), using 0.9-7.2 μg of DNA per 10 μl of tumor volume. In the case of delivery via PEI, amine:phosphate ratios of a range of 2.5:1 to 10.0:1 are suitable. A ratio of 7.5:1 was used in mouse trials. The PEI weight average molecular weights can be used in a range of about 10-50 kDa. A 25 kDa weight PEI was used in the mouse trials.

The chimeric gene construct was transfected at a transfection frequency of about 1-5 days. In the mouse model, the chimeric gene construct was transfected every 3 days. Maximal gene expression occurred 48-72 hours post-transfection. The activator was administered via i.p. or i.v. injection every day starting the day after the first transfection. Concentrations in the range of 0.1-10.0 mg/kg were used (2 mg/kg were used in mouse trials).

Figure 4A:
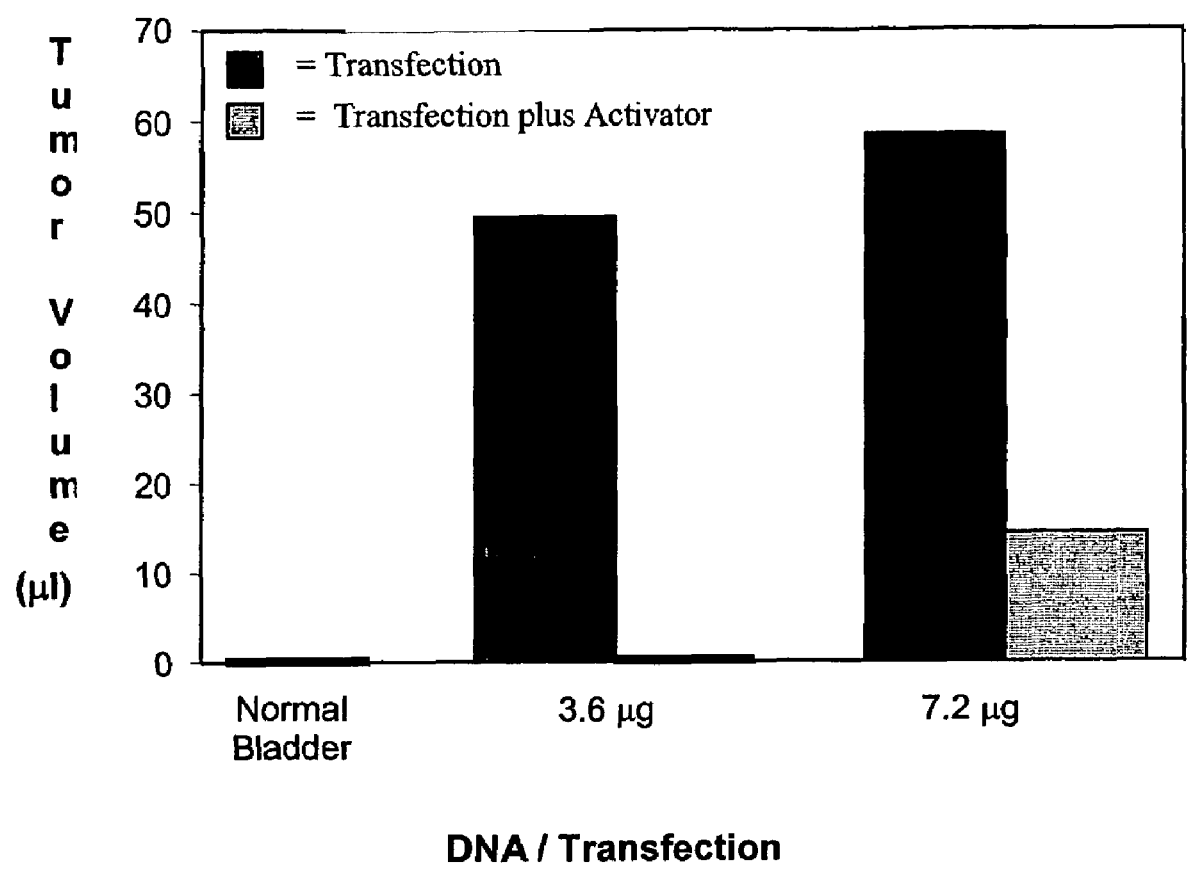
FIG. 4A is a bar chart depicting the effects of COX-2-caspase treatment on in vivo bladder tumor size after one week of treatment.
Figure 4B:
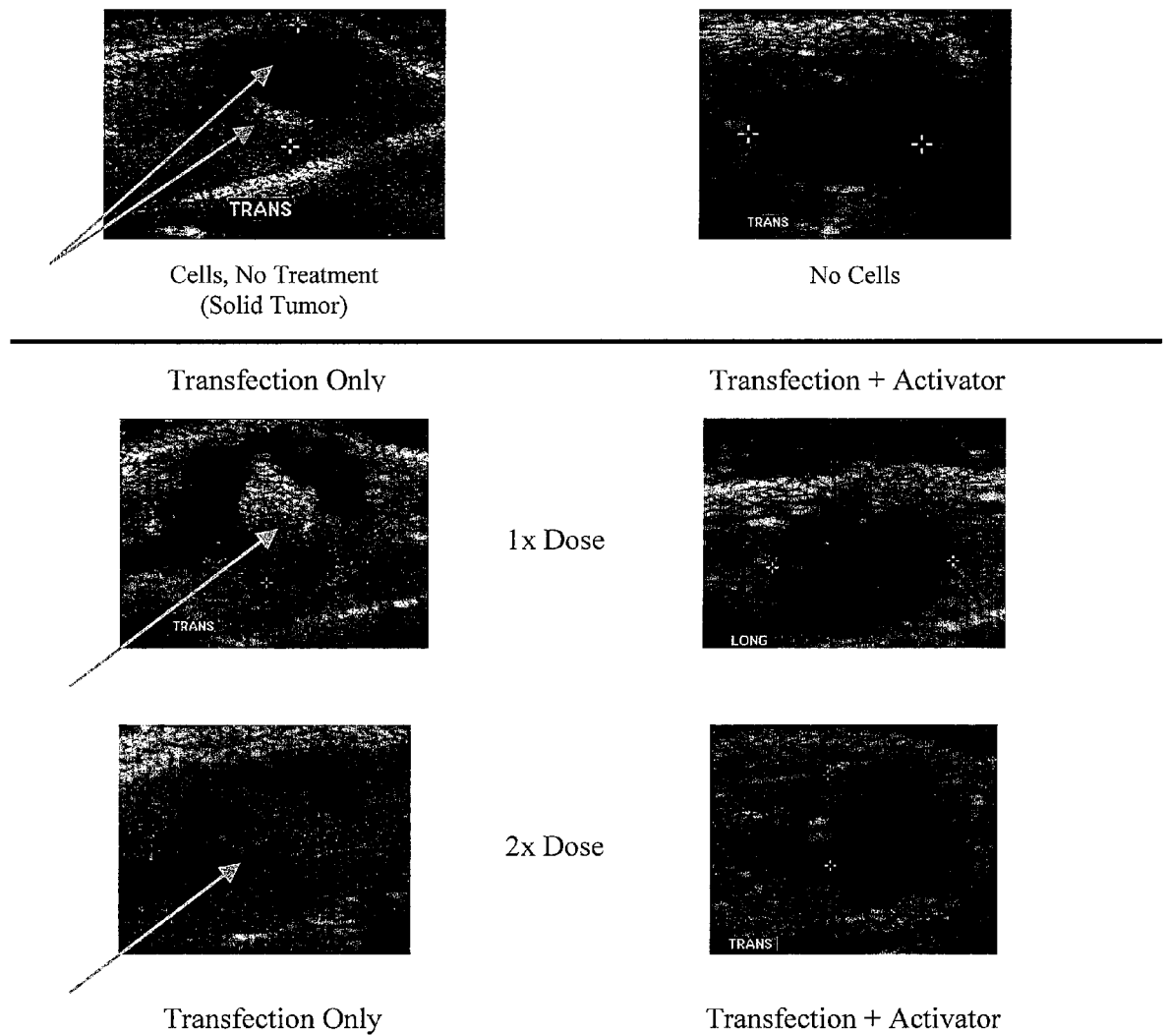
FIG. 4B shows images from ultrasound data showing the effects of COX-2-caspase treatment on in vivo bladder tumor size after one week of treatment.

The results showed great success in preventing the growth and spread of murine bladder tumors. Tumor progression was monitored via ultrasound, with results indicating tumor growth in all bladders except those treated with the full gene delivery/activation regimen and negative controls. FIG. 4A is a bar chart depicting the tumor volume after 1 week of treatment showing that mice transfected with the Cox-2-iCasp(3+9) genes, followed by the AP20187 activator, had small to nonexistant tumors, similar to normal bladders. The absence of activator yielded significant tumor growth. FIG. 4B is the ultrasound data taken after 1 week of treatment showing that mice transfected with the Cox-2-iCasp(3+9) genes developed solid bladder tumors similar to untreated controls, while mice receiving the same transfection complexes followed by activation of the caspase gene products had bladders with small to nonexistant tumors. The arrows indicate tumor tissue.

Figure 5A:
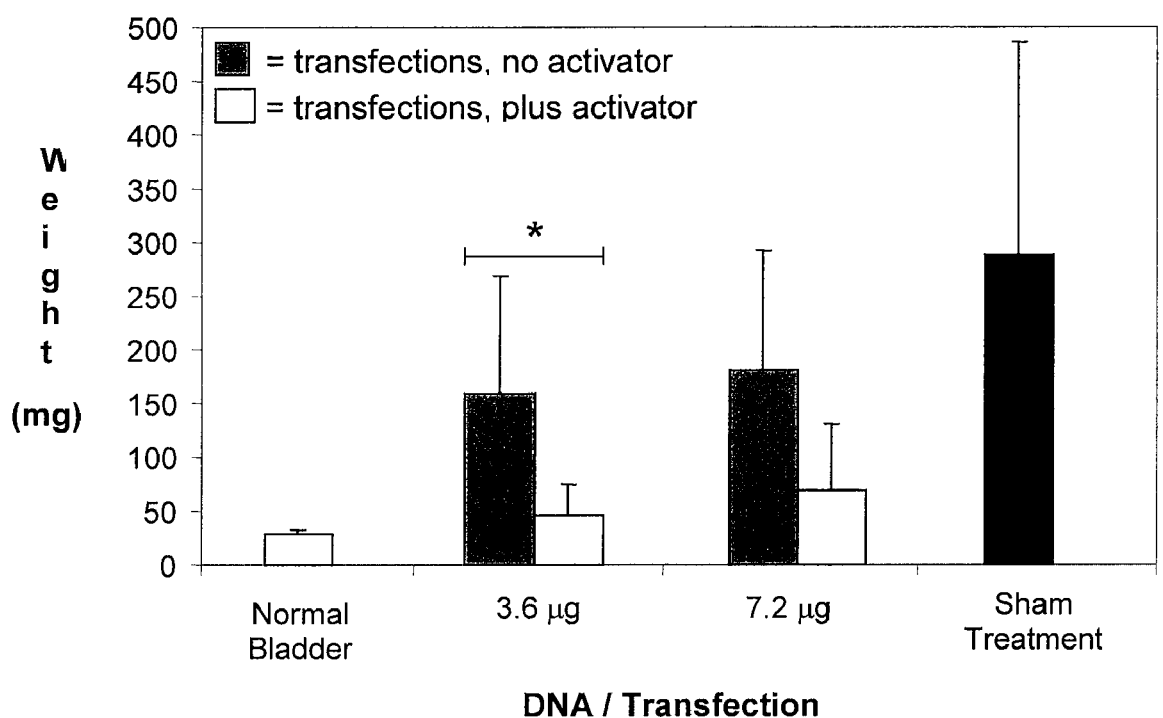
FIG. 5A is a bar chart of bladder weights comparing the effects of COX-2-caspase treatment with and without the addition of the AP20187 activator on in vivo bladder tumor size at 22-days following treatment.
Figure 5B:
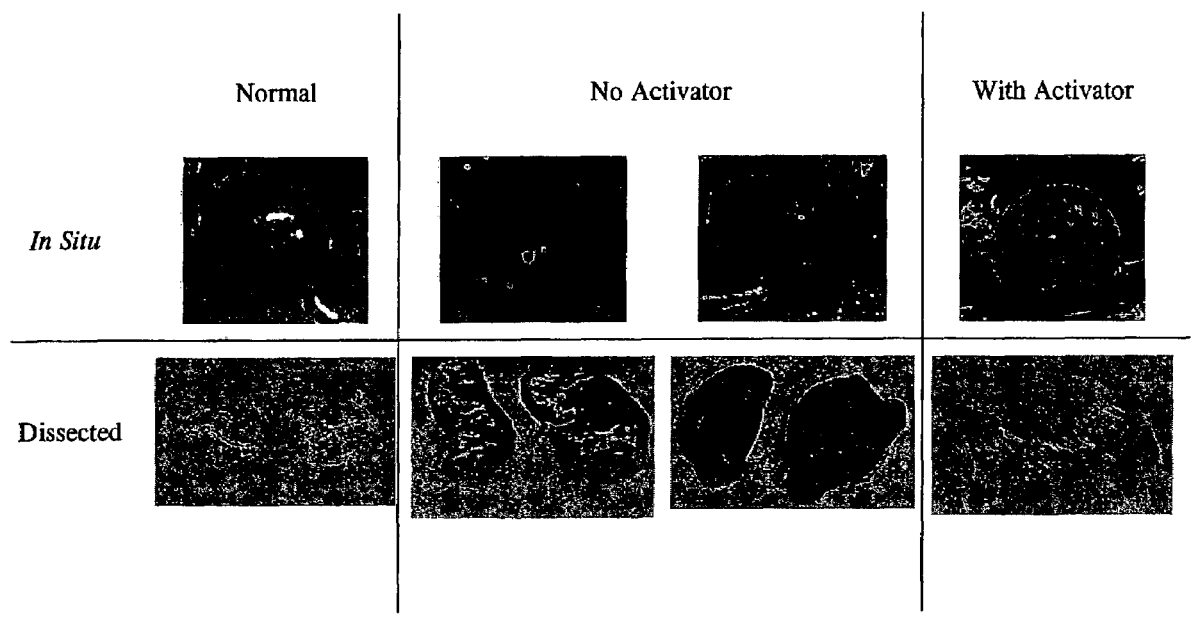
FIG. 5B shows gross examination of bladders illustrating the effects of COX-2-caspase treatment on in vivo bladder tumor size at 22-days following treatment.

Gross examination of bladders following the 22-day experimental course revealed similar findings in FIG. 5A. Bladder autopsies performed after 2 weeks of treatment show that mice transfected with the Cox-2-iCasp(3+9) genes, followed by the AP20187 activator, had bladder weights similar to normal bladders. The absence of activator yielded significant tumor growth. "*"=statistically significant difference between groups (student's t-test, p<0.05, n≧6). There was no difference between groups for normal and transfections involving activator (ANOVA, p>0.26), or between transfections without activator and sham-treated groups (ANOVA, p>0.40). This was further confirmed by visual bladder data taken after 2 weeks of treatment (shown in FIG. 5B) which shows that mice transfected with the Cox-2-iCasp(3+9) genes developed solid bladder tumors similar to untreated controls, while mice receiving the same transfection complexes followed by activation of the caspase gene products had bladders with small to nonexistant tumors. Whole bladders shown in FIG. 5B are approximately 14 mm in diameter.

Figure 6:
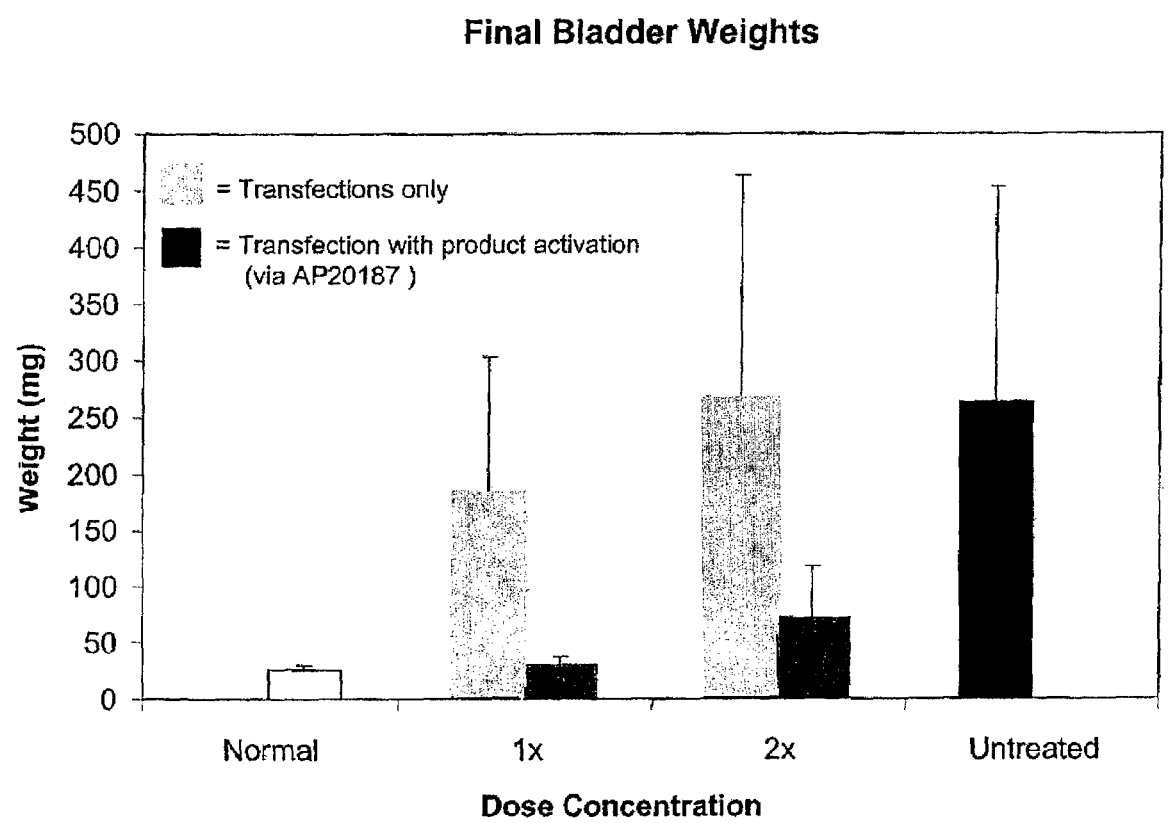
FIG. 6 is a bar graph showing the reduction in weight of isolated bladders treated with the methods of the invention.

Results that further characterize the system are shown in the bar graphs of FIGS. 6-9. FIG. 6 shows the results from experiments in which mouse bladders were innoculated with MB49 transitional cell carcinoma cells, then transfected with plasmids expressing caspases 3 and 9, under Cox-2 promotor control,. "Normal" bladders were used as a control, (white bar) while "untreated" bladders (black bar) received sham treatments with normal saline instead of the gene construct. Different dosages of the gene construct and carrier were delivered to each bladder. The treatments commenced after one week of tumor cell incubation, to allow the inoculated cells to develop into tumor tissue. Gene delivery took place on days 7, 10, 13, 16, and 19, with the delivery of the AP20187 agent via interperitoneal injection occurring daily on days 9-21. Ultrasound data were gathered on days 6, 14, and 21, and the animals were sacrificed for further study on day 22. The results show that there was no significant difference in bladder weight between the animals that received the 1× concentration (3.6 μg DNA/dose) of gene delivery complexes compared with those that received the 2× concentration (7.2 μg DNA/dose)of the same construct. The results also show that there was significant tumor growth, as determined by bladder weight, in bladders that did not receive the AP20187 compound which activated the caspase products of the delivered DNA constructs. In contrast, there was a reduction in tumor growth to normal in those bladders that received the compound in conjunction with the gene therapy. In at least one instance, tumor remission was observed (as observed via ultrasound).

Figure 7:
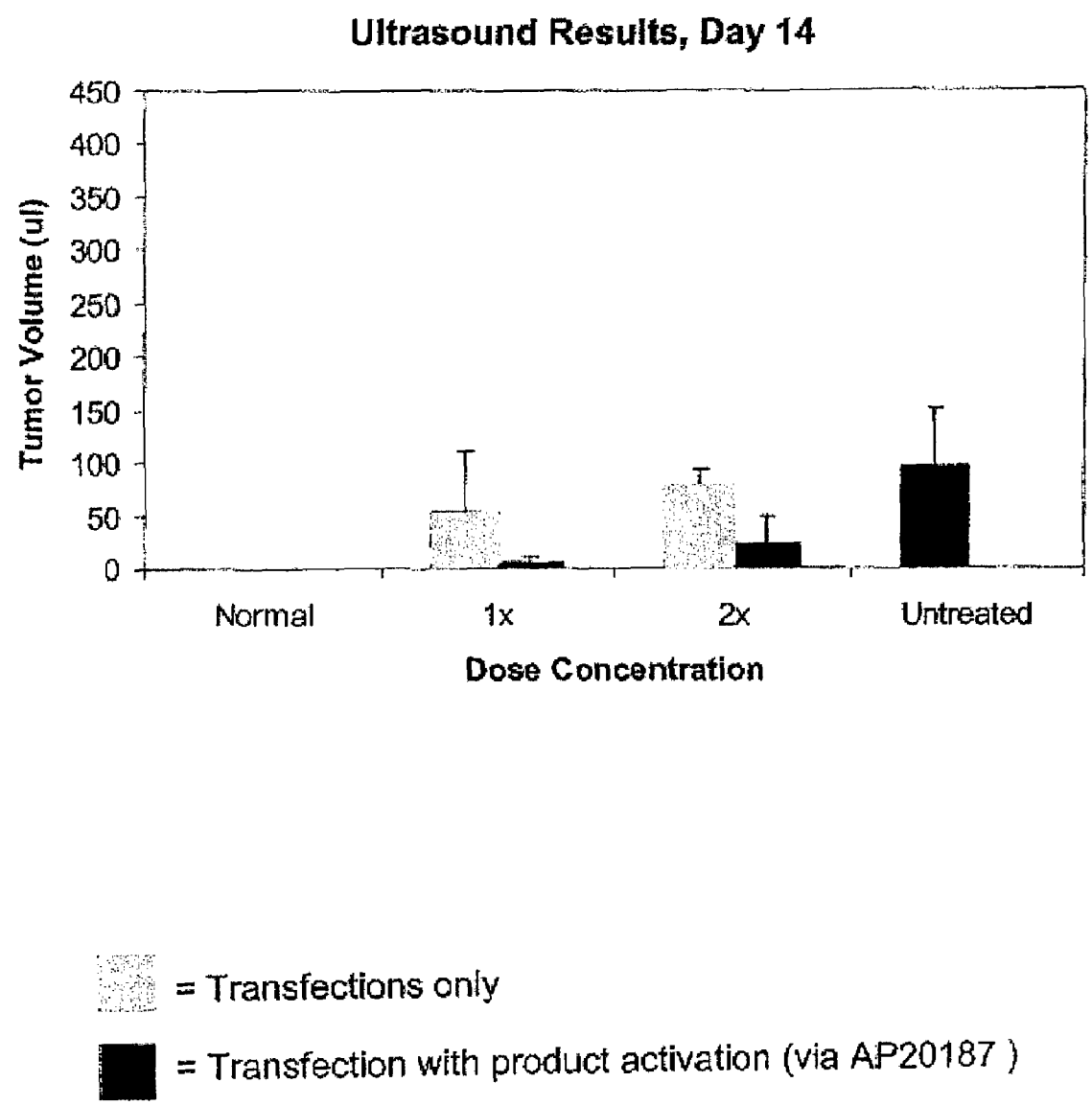
FIG. 7 is a bar graph showing the results of ultrasound studies of tumor volume at day 14 post incubation.
Figure 8:
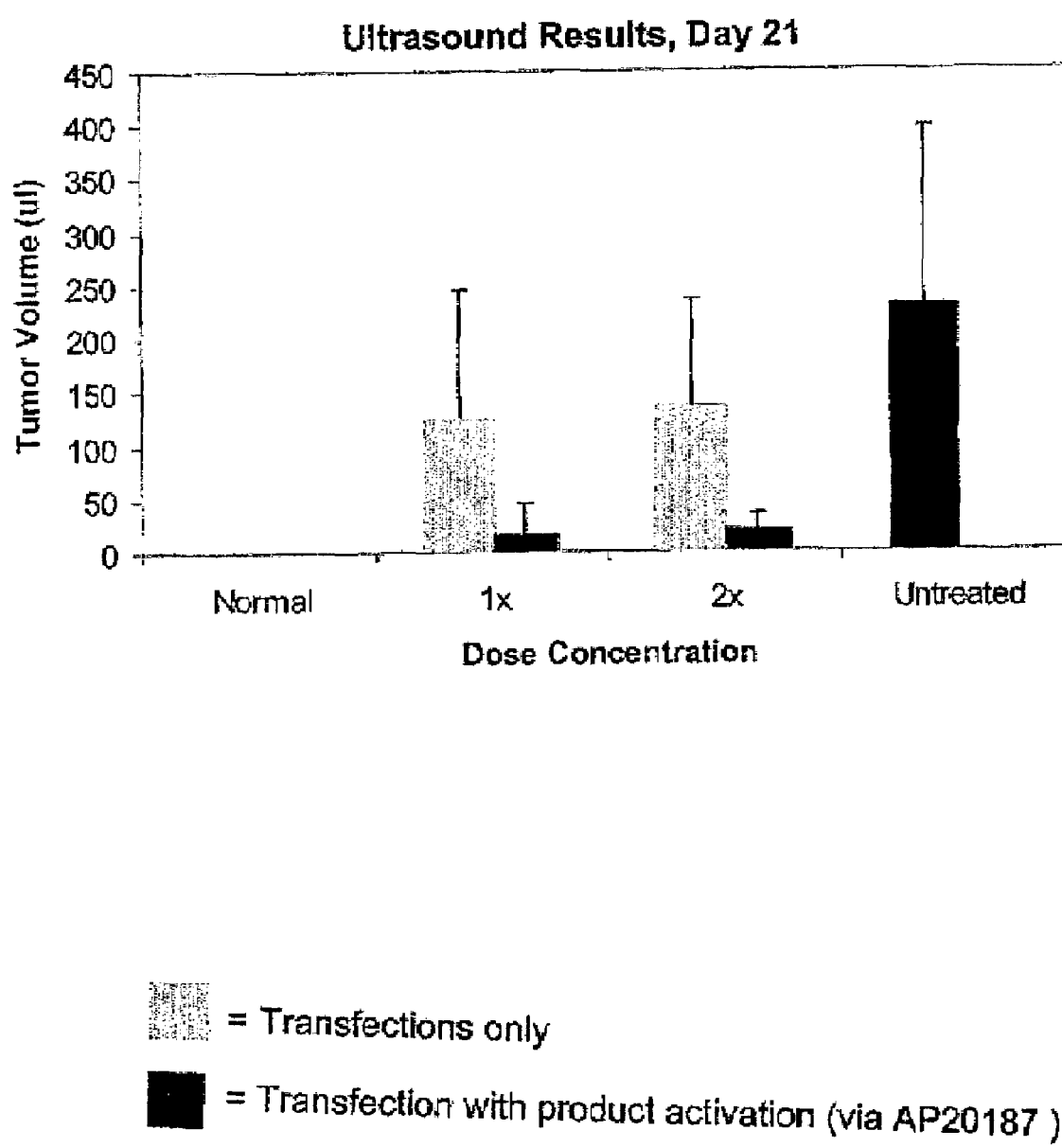
FIG. 8 is a bar graph showing the results of ultrasound studies of tumor volume at day 21 post incubation.
Figure 9:
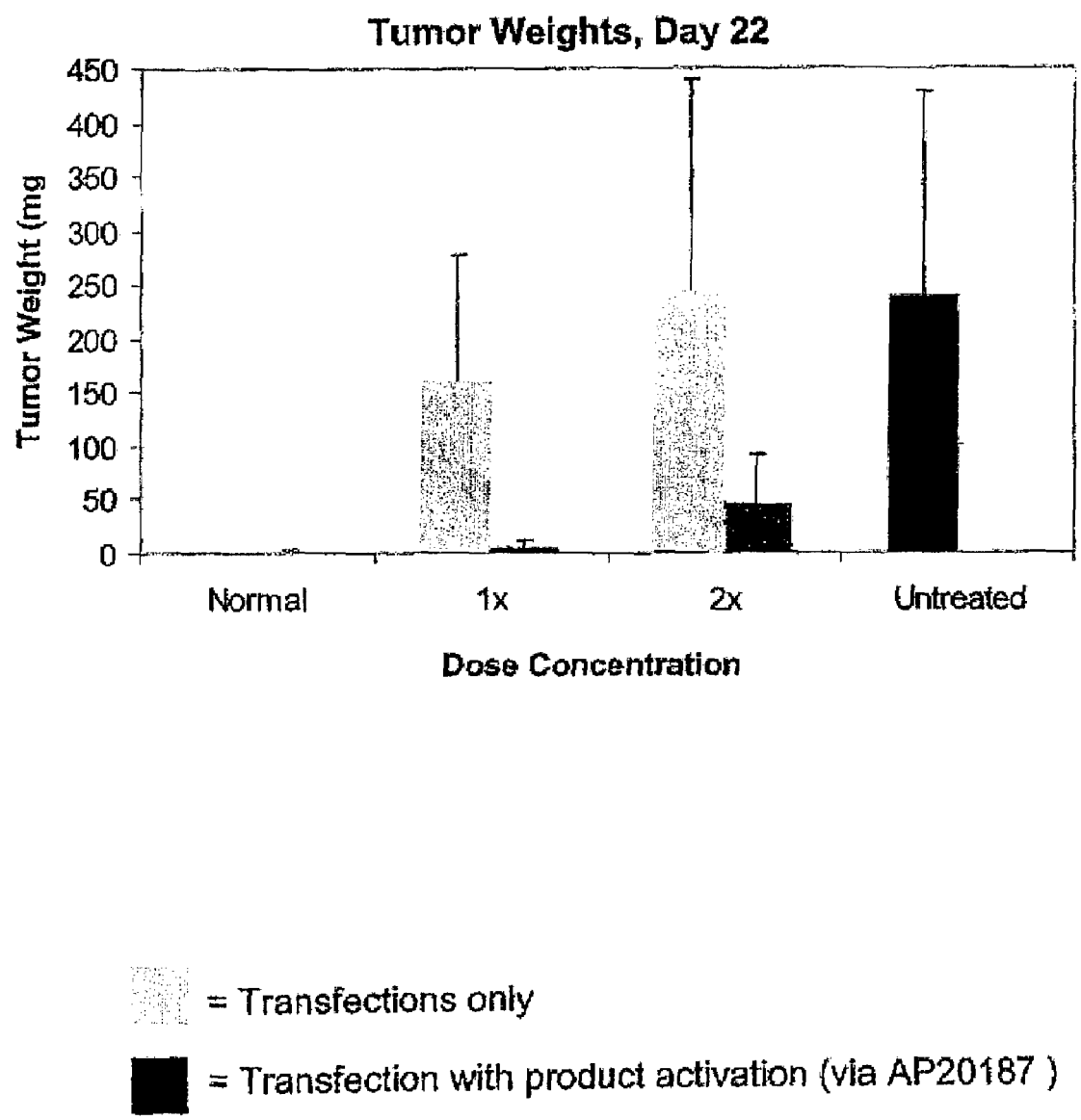
FIG. 9 is a bar graph showing the weight of isolated bladders at day 22.

FIGS. 7 and 8 depict the results of ultrasound studies measuring tumor volume on days 14 and 21, respectively. The results confirm that there is a reduction in tumor volume in those bladders that received the gene construct followed by AP20187 to activate the transfection products. FIG. 9 is a bar graph showing the tumor weight at day 22 after removal of the tumor. A comparison of the ultrasound study at day 21 (shown in FIG. 8) with the tumor weight at day 22 (shown FIG. 9) demonstrates the correlation between ultrasound and tumor weight data.

Collectively, the results reported here indicate that entire classes of cells can be treated via gene therapy that employs the judicious use of appropriate upstream binding elements for transcriptional control. It was shown that the phenomenon of COX-2 overexpression seen in numerous tumor types can be exploited to target the expression of delivered plasmids to such tumors, as was demonstrated in experiments utilizing cells of human bladder, prostate, and mammary cancers. Healthy, untransformed cells do not normally express COX-2, and did not express delivered COX-2-driven plasmids.

This work also served to further the concept of COX-2 promoter-targeting for cancer cells through the use of the targeting system in an in vitro application designed to bring about selective cell death through apoptosis. The non-viral polycation PEI was sufficient for gene delivery into cells and yielded transfection efficiencies typically in the range of 25-35% of cells expressing reporter. The use of inducible caspase technology served to demonstrate that either an initiator or an executioner caspase is sufficient by itself to trigger apoptotic cell death, even in certain apoptosis-resistant cancer cells. Such selective cell death is potentially applicable to precancerous cells, which are thought to overexpress COX-2 prior to their transformation.

The system described in the invention can be applied in the clinical setting for COX-2-overexpressing tumors, possibly via direct tumor injection or systemic administration of transfection complexes. Clinically, the described system may include a pre-treatment tumor analysis in order to confirm the presence of COX-2 overexpression. Despite the known COX-2 expression characteristics present in major tumor classes, COX-2 expression variability may occur between individual patients.

Example 8

Construction of a Vector with Active Apoptosis Inducing Genes

This example describes the investigation of selective expression of apoptosis-inducing genes in vitro using a construct that expresses caspases in the active form, thereby eliminating the need for an oligomerizing agent. In this example, the construct described in Example 1 was modified to remove the Fv' and $F_{vls}$ regions from the plasmid. These regions are responsible for producing an inducible caspase that requires a dimerizing agent, particularly, the AP20187 compound. By removing these regions, it removes the "inducible" portion of the inducible caspases, yielding plasmids that encode for active caspases. This procedure negates the need for a dimerizing agent to activate the caspases.

Figure 10:
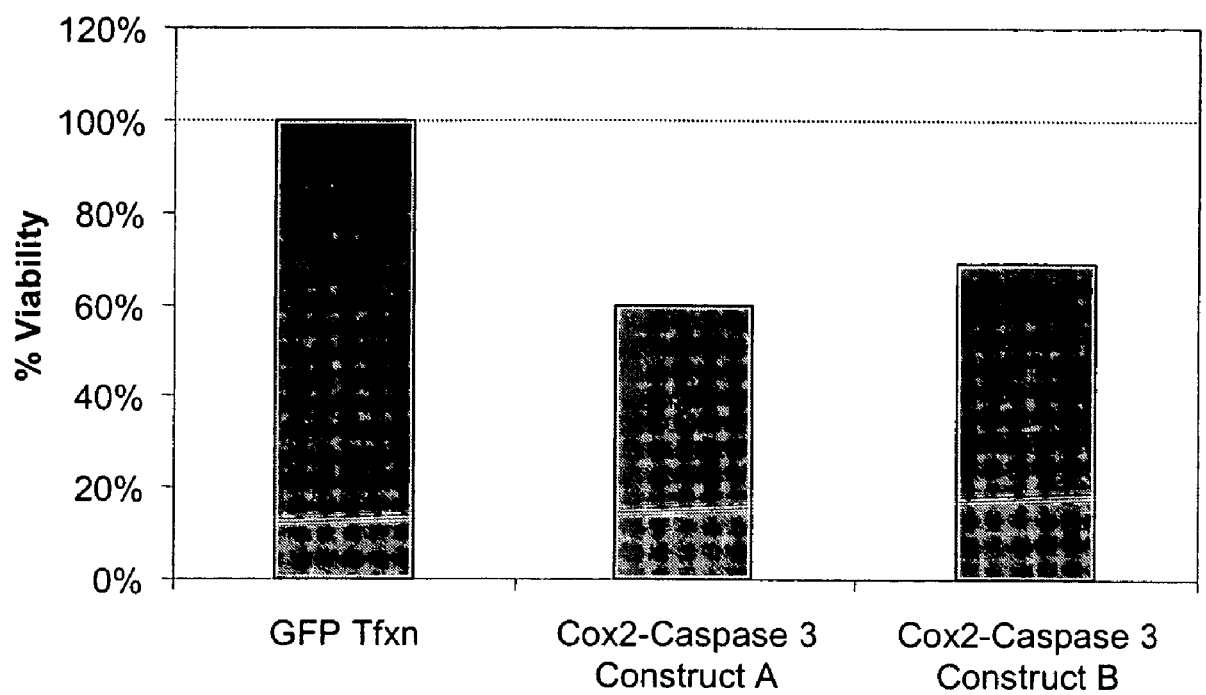
FIG. 10 is a bar graph showing % cell viability of cells transfected with an active COX-2-caspase 3 plasmid.

To examine the new constructs in vitro, MB49 cells (murine transitional cell carcinoma) were transfected one time with 3.6 or 7.2 μg of plasmid. The data, shown in FIG. 10, demonstrate that by removing the base sequences that require the use of a dimerizing agent from the existing COX-2-iCaspase 9 construct, the new constructs are responsible for between 30-40% cell mortality at 48 hours post-transfection (n=2). This is consistent with the % of cells that expressed the GFP reporter plasmid in the control wells.

The previous in vivo experiments used a combination of caspase 3- and caspase 9-related DNA (See example 7). In the present example, only a single COX-2-Caspase-3-coding plasmid was used. Further experiments are being conducted using the single COX-2-Caspase 9 clone, as well as experiments in which both the COX-2-Caspase-3-coding plasmid and the Cox2 Caspase-9-coding plasmid will be co-transfected. The results are likely to be even better with both caspases. In vivo expression of the construct is likely to produce the same results as those seen with the inducible caspases, described above.

Other embodiments and uses of the invention will be apparent to those skilled in the art from consideration of the specification and practice of the invention disclosed herein. All U.S. patents and other references noted herein for whatever reason are specifically incorporated by reference. The specification and examples should be considered exemplary only with the true scope and spirit of the invention indicated by the following claims.

What is claimed is:

1. A method of causing apoptosis in a diseased cell that overexpresses a protein, the method comprising delivering a chimeric gene construct to the cell, wherein the chimeric gene construct comprises an upstream regulatory element, which is activated by the protein overexpressed in the cell, operably linked to genes that encode Caspase-3 and Caspase-9, and expressing Caspase-3 and Caspase-9 in the cell that overexpresses the protein, wherein the combined production of Caspase-3 and Caspase-9 causes the cell to undergo apoptosis.

2. The method of claim 1, wherein the step of delivering the chimeric gene construct to the cell comprises delivering the chimeric gene construct by a non-viral delivery vehicle.

3. The method of claim 2, wherein the non-viral delivery vehicle is selected from the group consisting of poly(ethylenimine), lipofectin, lipofectamine, polylysine, and alginate.

4. The method of claim 2, wherein the non-viral delivery vehicle is poly(ethylenimine).

5. The method of claim 1, wherein the step of delivering the chimeric gene construct to the cell comprises delivering the chimeric gene construct by a viral delivery vehicle.

6. The method of claim 5, wherein the viral delivery vehicle is a viral vector selected from the group consisting of an adenovirus, an adeno-associated virus, a lentivirus and a retrovirus.

7. The method of claim 1, wherein the upstream regulatory element is selected from the group consisting of an cyclooxygenase promoter, a tumor necrosis factor promoter, an interleukin-2 promoter, an interleukin-21 promoter, and an interleukin-23 promoter.

8. The method of claim 1, wherein the protein which activates the upstream regulatory element is selected from the group consisting of a tumor necrosis factor, an interleukin-2, an interleukin-21, and an interleukin-23.

9. The method of claim 1, wherein the diseased cell is selected from the group consisting of a cancer cell, a tumor cell, and an inflammatory cell.

10. The method of claim 1, wherein the method further comprises expressing at least one additional gene for production of an apoptosis agent selected from the group consisting of Caspase-1, Caspase-2, Caspase-4, Caspase-5, Caspase-6, Caspase-7, Caspase-8, Caspase-10, Granzyme A, Granzyme B, Fas ligand, TRAIL and APO3L.

11. The method of claim 1, further comprising delivering to the cell an oligomerizing agent selected from the group consisting of a cyclosporin A-type ligand, a tetracycline, a steroid ligand, a Tet-On/Tet-Off system, an ecdysone-dimerizer system, an antiprogestin-dimerizer system, and a courmarin-dimerizer system.

12. A method of causing apoptosis in a diseased cell that overexpresses cyclooxygenase-2, the method comprising delivering a chimeric gene construct to the cell, wherein the chimeric gene construct comprises a cyclooxygenase-2 promoter, which is activated by the cyclooxygenase-2, operably linked to genes that encode for production of Caspase-3 and Caspase-9, and expressing Caspase-3 and Caspase-9 in the diseased cell that overexpresses cyclooxygenase-2, wherein the combined production of Caspase-3 and Caspase-9 causes the cell to undergo apoptosis.

13. The method of claim 12, wherein the step of delivering the chimeric gene construct to the cell comprises delivering the chimeric gene construct by a non-viral delivery vehicle.

14. The method of claim 13, wherein the non-viral delivery vehicle is selected from the group consisting of poly(ethylenimine), lipofectin, lipofectamine, polylysine, and alginate.

15. The method of claim 13, wherein the non-viral delivery vehicle is poly(ethylenimine).

16. The method of claim 12, wherein the step of delivering the chimeric gene construct to the cell comprises delivering the chimeric gene construct by a viral delivery vehicle.

17. The method of claim 16, wherein the viral delivery vehicle is a viral vector selected from the group consisting of an adenovirus, an adeno-associated virus, a lentivirus, and a retrovirus.

18. The method of claim 12, wherein the diseased cell is selected from the group consisting of a cancer cell, a tumor cell and an inflammatory cell.

19. The method of claim 12, wherein the method further comprises expressing at least one additional gene for production of an apoptosis agent selected from the group consisting of Caspase-1, Caspase-2, Caspase-4, Caspase-5, Caspase-6, Caspase-7, Caspase-8, Caspase-10, Granzyme A, Granzyme B, Fas ligand, TRAIL and APO3L.

20. The method of claim 12, further comprising delivering to the cell an oligomerizing agent.

21. A method of causing apoptosis in a diseased cell that overexpresses a protein, the method comprising delivering a first and a second chimeric gene construct to the cell, wherein the first chimeric gene construct comprises an upstream regulatory element, which is activated by the protein overexpressed in the cell, operably linked to a Caspase-3 gene and the second chimeric gene construct comprises the upstream regulatory element operably linked to a Caspase-9 gene, and expressing Caspase-3 and Caspase-9 in the cell that overexpresses the protein, wherein the combined production of Caspase-3 and Caspase-9 causes the cell to undergo apoptosis.

22. The method of claim 21, wherein the step of delivering the chimeric gene constructs to the cell comprises delivering the chimeric gene constructs by a non-viral delivery vehicle.

23. The method of claim 22, wherein the non-viral delivery vehicle is selected from the group consisting of poly(ethylenimine), lipofectin, lipofectamine, polylysine, and alginate.

24. The method of claim 22, wherein the non-viral delivery vehicle is poly(ethylenimine).

25. The method of claim 21, wherein the step of delivering the chimeric gene constructs to the cell comprises delivering the chimeric gene constructs by a viral delivery vehicle.

26. The method of claim 25, wherein the viral delivery vehicle is a viral vector selected from the group consisting of an adenovirus, an adeno-associated virus, a lentivirus, and a retrovirus.

27. The method of claim 21, wherein the upstream regulatory element is selected from the group consisting of an cyclooxygenase promoter, a tumor necrosis factor promoter, an interleukin-2 promoter, an interleukin-21 promoter, and an interleukin-23 promoter.

28. The method of claim 21, wherein the protein which activates the upstream regulatory element is selected from the group consisting of a tumor necrosis factor, an interleukin-2, an interleukin-21, and an interleukin-23.

29. The method of claim 21, wherein the diseased cell is selected from the group consisting of a cancer cell, a tumor cell, and an inflammatory cell.

30. The method of claim 21, wherein the method further comprises expressing at least one additional gene for production of an apoptosis agent selected from the group consisting of Caspase-1, Caspase-2, Caspase-4, Caspase-5, Caspase-6, Caspase-7, Caspase-8, Caspase-10, Granzyme A, Granzyme B, Fas ligand, TRAIL and APO3L.

31. The method of claim 21, further comprising regulating apoptosis using an oligomerizing agent selected from the group consisting of a cyclosporin A-type ligand, a tetracycline, a steroid ligand, a Tet-On/Tet-Off system, an ecdysone-dimerizer system, an antiprogestin-dimerizer system, and a courmarin-dimerizer system.

32. A method of causing apoptosis in a diseased cell that overexpresses cyclooxygenase-2, the method comprising delivering a first and a second chimeric gene construct to the cell, wherein the first chimeric gene construct comprises a cyclooxygenase-2 promoter, which is activated by the protein overexpressed in the cell, operably linked to a Caspase-3 gene and the second chimeric gene construct comprises the cyclooxygenase-2 promoter operably linked to a Caspase-9 gene, and expressing Caspase-3 and Caspase-9-in the diseased cell that overexpresses cyclooxygenase-2, wherein the combined production of Caspase-3 and Caspase-9 causes the cell to undergo apoptosis.

33. The method of claim 32, wherein the step of delivering the chimeric gene construct to the cell comprises delivering the chimeric gene construct by a non-viral delivery vehicle.

34. The method of claim 33, wherein the non-viral delivery vehicle is selected from the group consisting of poly(ethylenimine), lipofectin, lipofectamine, polylysine, and alginate.

35. The method of claim 33, wherein the non-viral delivery vehicle is poly(ethylenimine).

36. The method of claim 32, wherein the step of delivering the chimeric gene construct to the cell comprises delivering the chimeric gene construct by a viral delivery vehicle.

37. The method of claim 36, wherein the viral delivery vehicle is a viral vector selected from the group consisting of an adenovirus, an adeno-associated virus, a lentivirus, and a retrovirus.

38. The method of claim 32, wherein the diseased cell is selected from the group consisting of a cancer cell, a tumor cell and an inflammatory cell.

39. The method of claim 32, wherein the method further comprises expressing at least one additional gene for production of an apoptosis agent selected from the group consisting of Caspase-1, Caspase-2, Caspase-4, Caspase-5, Caspase-6, Caspase-7, Caspase-8, Caspase-10, Granzyme A, Granzyme B, Fas ligand, TRAIL and APO3L.

40. The method of claim 32, further comprising delivering to the cell an oligomerizing agent.

* * * * *

UNITED STATES PATENT AND TRADEMARK OFFICE
CERTIFICATE OF CORRECTION

PATENT NO. : 7,638,331 B2
APPLICATION NO. : 11/023020
DATED : December 29, 2009
INVENTOR(S) : W. T. Godbey and Anthony Atala It is certified that error appears in the above-identified patent and that said Letters Patent is hereby corrected as shown below:

On the title page item (73), Assignee: The name is listed as "The Administration of the Tulane Rducation Fund". The name should be corrected to read "The Administration of the Tulane Education Fund".

Signed and Sealed this

Ninth Day of February, 2010

David J. Kappos
*Director of the United States Patent and Trademark Office*

UNITED STATES PATENT AND TRADEMARK OFFICE
CERTIFICATE OF CORRECTION

PATENT NO.      : 7,638,331 B2                                              Page 1 of 1
APPLICATION NO. : 11/023020
DATED           : December 29, 2009
INVENTOR(S)     : Godbey et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 929 days.

Signed and Sealed this

Ninth Day of November, 2010

David J. Kappos
*Director of the United States Patent and Trademark Office*